United States Patent
Sakanoue et al.

(10) Patent No.: US 8,071,712 B2
(45) Date of Patent: Dec. 6, 2011

(54) MULTIBRANCHED POLYOXYALKYLENE DERIVATIVE

(75) Inventors: Kenji Sakanoue, Kawasaki (JP); Hiroki Yoshioka, Kawasaki (JP); Tomohiro Shirosaki, Kawasaki (JP)

(73) Assignee: NOF Corporation, Tokyo (JP)

( * ) Notice: Subject to any disclaimer, the term of this patent is extended or adjusted under 35 U.S.C. 154(b) by 277 days.

(21) Appl. No.: 12/529,043

(22) PCT Filed: Feb. 28, 2008

(86) PCT No.: PCT/JP2008/053568
§ 371 (c)(1),
(2), (4) Date: Aug. 28, 2009

(87) PCT Pub. No.: WO2008/105514
PCT Pub. Date: Sep. 4, 2008

(65) Prior Publication Data
US 2010/0029899 A1  Feb. 4, 2010

(30) Foreign Application Priority Data
Feb. 28, 2007  (JP) .................. 2007-050782

(51) Int. Cl.
*C08G 65/34* (2006.01)
(52) U.S. Cl. ........ 528/425; 564/505; 568/624; 568/623; 560/198
(58) Field of Classification Search .......... 564/505; 568/624, 623; 560/198; 528/425
See application file for complete search history.

(56) References Cited

FOREIGN PATENT DOCUMENTS

| JP | 7-216095 A | 8/1995 |
| JP | 9-302087 A | 11/1997 |
| JP | 2000-001542 A | 1/2000 |
| JP | 2000001542 A * | 1/2000 |
| JP | 2000-44674 A | 2/2000 |
| JP | 2004-197077 A | 7/2004 |
| JP | 2005-514505 A | 5/2005 |
| JP | 2007-503514 A | 2/2007 |

OTHER PUBLICATIONS

International Search Report issued in PCT/JP2008/053568 dated Apr. 22, 2008.
International Preliminary Examination Report (PCT/ISA/237) issued in PCT/JP2008/053568 dated Apr. 22, 2008.

\* cited by examiner

Primary Examiner — Randy Gulakowski
Assistant Examiner — Shane Fang
(74) Attorney, Agent, or Firm — Sughrue Mion, PLLC

(57) ABSTRACT

An object of the present invention is to provide a novel multibranched polyoxyalkylene derivative, and an intermediate for the production thereof. Specifically, the object is to provide a multibranched polyoxyalkylene derivative which can keep a high activity of a bio-related substance modified with the multibranched polyoxyalkylene derivative and which can easily produce the modified substance; an intermediate thereof; and a bio-related substance to which the multibranched polyoxyalkylene derivative is bonded. The novel multibranched polyoxyalkylene derivative according to the invention is a polyoxyalkylene derivative (1) having a functional group reactive with a bio-related substance and the bio-related substance according to the invention has a structure modified with the above polyoxyalkylene derivative (1) by a reaction. Furthermore, the intermediate for the production of the novel multibranched polyoxyalkylene derivative according to the invention is a polyoxyalkylene derivative (A).

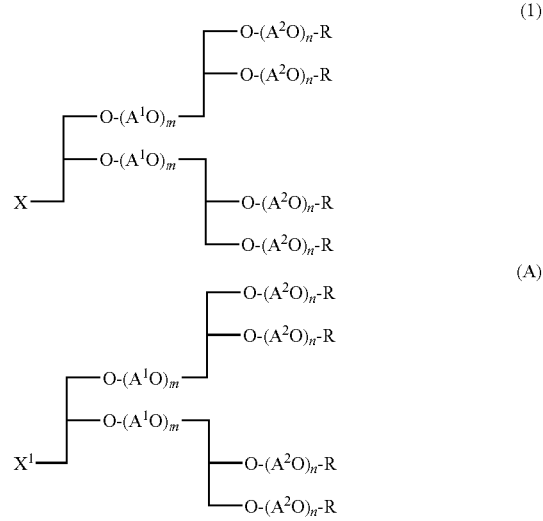

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, X represents a functional group reactive with a bio-related substance, and $X^1$ represents a hydroxyl group which may be protected.

5 Claims, No Drawings

MULTIBRANCHED POLYOXYALKYLENE DERIVATIVE

TECHNICAL FIELD

The present invention relates to a multibranched polyoxyalkylene derivative to be used in use applications which involve modification of bio-related substances, and an intermediate for producing the multibranched reactive polyoxyalkylene derivative. Furthermore, it relates to a modified bio-related substance to which the polyoxyalkylene derivative is bonded.

BACKGROUND ART

With the advance in genetic engineering, recently, development and studies on medicaments have been actively carried out, which use bio-related substances such as intercellular signaling substances such as hormones and cytokines, antibodies, and enzymes. Since these bio-related substances are usually cleared from the body because of the filtration through glomeruli in the kidney and the uptake by macrophages in the liver, spleen, and the like when the substances are injected to a living body, they have short half-lives in blood and hence it is difficult to obtain a sufficient pharmacological effect. For solving the problems, it is attempted to improve the behavior in a living body by encapsulating the bio-related substances in liposomes or polymer micelles or increasing their molecular weight or formation of a hydration layer through chemical modification with an amphiphatic polymer such as a sugar chain or polyethylene glycol or albumin. Moreover, by the modification with polyoxyalkylene, effects of decreasing toxicity and antigenicity and enhancing solubility of sparingly water-soluble pharmaceuticals are also obtained.

Recently, in the case of modifying a bio-related substance with polyoxyalkylene, in order not to block the active site or in order to obtain a larger hydration layer with lesser number of polyoxyalkylene, increase in molecular weight of a polyoxyalkylene derivative has been investigated. However, in the case of producing high-molecular-weight polyoxyalkylene, there arise problems in production, such as decrease in purity and increase in viscosity, and thus polyoxyalkylene suitable for a modifier of the bio-related substance is not efficiently obtained.

On the other hand, in order to perform more effective increase in molecular weight, development of the use of polyoxyethylene having a branched structure has been advanced. Patent Document 1 describes asparaginase using polyoxyalkylene having a double-chain structure containing cyanuric chloride as a main skeleton and Patent Document 2 describes interferon-α using polyoxyalkylene having a double-chain structure containing lysine as a main skeleton. Also, Patent Document 3 describes a bio-related substance using polyoxyalkylene having a double-chain structure containing 1,2-glycerol as a main skeleton.

These structures all have a double-chain structure as a basic skeleton but, in order to obtain a larger hydration layer, polyoxyalkylene having more highly branched structure has been required from the viewpoint of developing medical uses.

Patent Documents 4 and 5 describe polyoxyalkylene derivatives having tri- to penta-branched structure containing a cyclohexane ring, a monosaccharide such as glucose or sorbitol, or a polycarboxylic acid such as citric acid as a basic skeleton and Patent Documents 6 and 7 describe a polyoxyalkylene derivative having a quadruple-chain structure containing triglycerin as a basic skeleton.

Since the polyoxyalkylene derivatives described in Patent Documents 4 and 5 is produced by introduction to the basic skeleton such as a cyclic polyol by reacting an excess amount of a single-chain polyoxyalkylene derivative, excess single-chain polyoxyalkylene derivative not reacted with the basic skeleton remains and thus it should be removed. Moreover, when the number of the target polyoxyalkylene chains is a large number, since impurities wherein the target number of the chains has not been introduced are produced as by-products, it is very difficult to diminish these impurities and thus industrial production thereof is further difficult.

The polyoxyalkylene derivatives described in Patent Documents 6 and 7 are obtained by adding ethylene oxide to triglycerin monoallyl ether. However, in the case where an alkali is used as a catalyst for the addition reaction, the allyl ether is rearranged into a propenyl ether and, further in the case where an acid is used in a neutralization step or the like, the system becomes locally acidic and the propenyl ether is converted into a hydroxyl group, so that purity of the target product becomes low. Moreover, in Patent Documents 6 and 7, a carboxyl group or an amino group is introduced though formation of a sulfide bond by the reaction of the allyl ether group with a carboxylic acid having a mercapto group or an organic amine having a mercapto group, so that the obtained compounds are limited to only those having a sulfide bond.

As above, a derivative having a multiple number of polyoxyalkylene chains which is capable of being effectively used in use applications which involve modification of bio-related substances and is industrially easily produced has not been obtained and it is highly desired to develop such a multibranched polyalkylene derivative.

Patent Document 1: Japanese Patent Application Laid-Open: JP-B-61-42558

Patent Document 2: Japanese Patent Application Laid-Open: JP-A-10-67800

Patent Document 3: Japanese Patent Application Laid-Open: JP-A-2004-197077

Patent Document 4: WO01/048052 pamphlet

Patent Document 5: WO02/060978 pamphlet

Patent Document 6: Japanese Patent Application Laid-Open: JP-A-2000-1542

Patent Document 7: Japanese Patent Application Laid-Open: JP-A-2000-44674

DISCLOSURE OF THE INVENTION

Problems that the Invention is to Solve

An object of the present invention is to provide a novel multibranched polyoxyalkylene derivative, and an intermediate for the production thereof. Specifically, the object is to provide a high-molecular-weight multibranched polyoxyalkylene derivative which can keep a high activity of a bio-related substance modified with the multibranched polyoxyalkylene derivative and which can easily produce the modified substance, an intermediate thereof, and a bio-related substance to which the multibranched polyoxyalkylene derivative is bonded.

Means for Solving the Problems

As a result of extensive studies for solving the above problems, the present inventors have devised a novel multi-branched polyoxyalkylene derivative and thus have accomplished the invention.

Namely, the invention relates to a multibranched polyoxyalkylene derivative having a reactive group at 1-position of glycerin and oxyalkylene chains at 2- and 3-positions thereof and having further multibranched structures by polyhydric alcohol skeletons at the terminal end of the oxyalkylene chains as shown in the formula (1A) as well as an intermediate for the production thereof. Furthermore, it relates to a bio-related substance modified with the poly(alkylene glycol) derivative.

Namely, the invention is as shown below.

[1] A polyoxyalkylene derivative represented by the formula (1A):

[Chem 1]

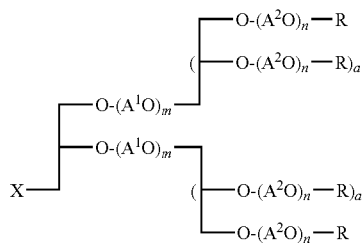
(1A)

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, X represents a functional group reactive with a bio-related substance, and a represents 1, 3, or 5.

[2] A polyoxyalkylene derivative represented by the formula (1):

[Chem 2]

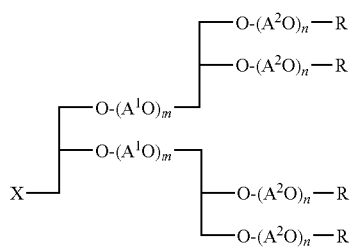
(1)

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, and X represents a functional group reactive with a bio-related substance.

[3] A bio-related substance modified by the reaction with the polyoxyalkylene derivative represented by the formula (1A).

[4] A polyoxyalkylene derivative represented by the formula (1B):

[Chem 3]

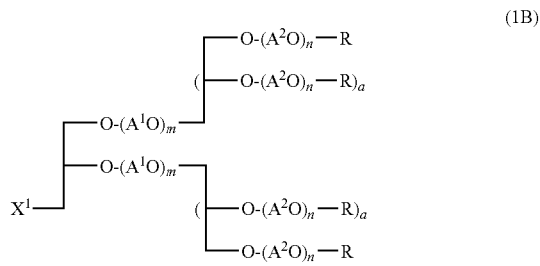
(1B)

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, $X^1$ represents a hydroxyl group which may be protected, and a represents 1, 3, or 5.

[5] A polyoxyalkylene derivative represented by the formula (A):

[Chem 4]

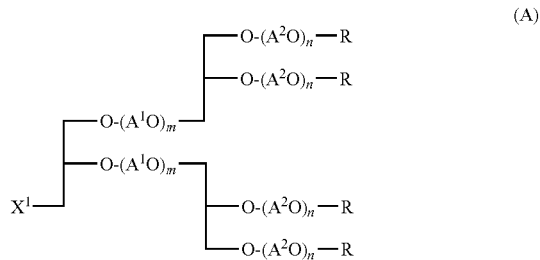
(A)

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, and $X^1$ represents a hydroxyl group which may be protected.

ADVANTAGE OF THE INVENTION

The novel multibranched polyoxyalkylene derivative (1A) according to the present invention can afford a large hydration layer with maintaining an active site of a bio-related substance since the derivative has a multibranched structure, and also the derivative does not decreases the activity of the bio-related substance bonded thereto. Furthermore, by increasing the branches of the polyoxyalkylene derivative having the multibranched structure, viscosity can be reduced. As advantages of the reduction of the viscosity, there may be, for example, mentioned easiness of handling of the derivative at the time when it is used for modification of a bio-related substance and more specifically, there may be mentioned the capability of reducing the pressure required for injection, the capability of relieving pain at injection, and the like. Moreover, there may be also mentioned as an advantage the capability of producing the derivative in a good purity without problem in production also by performing procedures, which are known per se, stepwisely.

Furthermore, since the derivative has a double-chain structure having a specific molecular weight between the functional group capable of forming a chemical bond with a bio-related substance and the multibranched structure, the reactivity between the bio-related substance and the multibranched polyoxyalkylene derivative (1A) can be improved.

According to the invention, a novel multibranched polyoxyalkylene derivative having such characteristics and an intermediate thereof can be provided.

BEST MODE FOR CARRYING OUT THE INVENTION

In the specification, a of the polyoxyalkylene derivative represented by the formula (1A) is 1, 3, or 5 and is preferably 1 or 3. Particularly, from the viewpoint that the impurities formed in the progress of the production can be further diminished, one wherein a is 1, i.e., a polyoxyalkylene derivative represented by the formula (1) is preferred.

In the specification, $A^1O$ and $A^2O$ each independently represents an oxyalkylene group having 2 to 4 carbon atoms. Specifically, it includes oxyalkylene groups having 2 to 4 carbon atoms, preferably 2 to 3 carbon atoms, such as an oxyethylene group, an oxypropylene group, an oxytrimethylene group, an oxy-1-ethylethylene group, an oxy-1,2-dimethylethylene group, and an oxytetramethylene group. The oxyalkylene groups may be the same or different from each other in $A^1O$ and $A^2O$ and may be added randomly or blockwise. In general, the fewer the carbon atoms are, the higher the hydrophilicity is. The group is preferably an oxyethylene group or an oxypropylene group, more preferably an oxyethylene group.

In the specification, m and n are each an average number of moles of the oxyalkylene group added. m is 20 to 500, preferably 40 to 300, more preferably 50 to 230, further preferably 80 to 150 and n is 15 to 700, preferably 50 to 700, more preferably 80 to 500, further preferably 100 to 350.

The molecular weight of the double-chain structure part ($A^1O$ chain) is 2,000 to 40,000, preferably 5,000 to 25,000, further preferably 8,000 to 15,000.

In the case where a is 1, 3, or 5, the molecular weight of the part of the multiple-chain structure ($A^2O$ chain) is 3,000 to 80,000, preferably 10,000 to 75,000, further preferably 20,000 to 65,000.

The molecular weight of the multibranched polyoxyalkylene derivative (1A) varies depending on the kind of the "functional group reactive with a bio-related substance" but is usually 5,000 to 120,000, preferably 20,000 to 100,000, further preferably 30,000 to 80,000.

The molecular weight of the polyoxyalkylene derivative (1B) is usually 5,000 to 120,000, preferably 20,000 to 100,000, further preferably 30,000 to 80,000.

Moreover, with regard to the ratio of the molecular weight of the double-chain structure part ($A^1O$ chain) to that of the multiple-chain part ($A^2O$ chain), when the molecular weight of the double-chain structure part ($A^1O$ chain) is regarded as 1, in the case where a is 1, 3, or 5, the molecular weight of the multiple-chain part ($A^2O$ chain) is 1 to 40, preferably 1.5 to 10, further preferably 2 to 5.

The "functional group reactive with a bio-related substance" which is represented by X in the multibranched polyoxyalkylene derivative of the formula (1) is not particularly limited as far as it is a functional group reactive with a bio-related substance and a group capable of forming a chemical bond. In this connection, a sulfide bond is preferably not contained in the binding part between the polyoxyalkylene chain and the functional group. This is because the stability of the bond tends to become worse when a sulfide bond is contained in the binding part.

The functional group may be bonded to the bio-related substance through a linker and therefore the "functional group reactive with a bio-related substance" represented by X is a concept that also includes the linker part.

In a preferable embodiment, X is a group represented by the group (I):

Group (I):

[Chem 5]

(a) -Z-NH$_2$ (b) -Z-N(maleimide group, 2,5-dioxo-2,5-dihydro-1H-pyrrol-1-yl)

(c) -Z-CO-N(succinimide group, 2,5-dioxopyrrolidin-1-yl)

(d) —O—CO—C$_6$H$_4$—NO$_2$ (e) —O—C(=O)—CH$_2$—W$^1$ (f) -Z-C(=O)—NHNH$_2$ (g) -Z-ONH$_2$ (h) -Z-COOH (i) -Z-SH (j) -Z-CH(=O)

(k) —O—C(=O)—N(imidazol-1-yl)

(l) —O—CO—N(benzotriazol-1-yl)

(m) —O—S(=O)$_2$—R$^1$

-Z-C≡CH     (n)

-Z-N₃     (o)

wherein $R^1$ represents a hydrocarbon group having 1 to 10 carbon atoms which may contain fluorine atoms, $W^1$ represents a halogen atom, and Z represents a linker between the poly(alkylene glycol)-oxy group and the functional group.

The groups represented by (c), (d), (h), (j), (k), and (l) are preferable in the case of the reaction with an amino group of the bio-related substance, the groups represented by (b), (c), (d), (e), (h), (i), (j), (k), (l), and (n) are preferable in the case of the reaction with a mercapto group of the bio-related substance, the groups represented by (i) and (o) are preferable in the case of the reaction with an unsaturated bond of the bio-related substance, and the groups represented by (a), (g), and (i) are preferable in the case of the reaction with a carboxyl group of the bio-related substance, and the groups represented by (a), (f), (g), and (i) are preferable in the case of the reaction with an aldehyde group of the bio-related substance, and the group represented by (n) is preferable in the case of the reaction with an azide bond of the bio-related substance. The group represented by (m) is used as a reaction intermediate.

Z in the group (I) is a linker between the poly(alkylene glycol)-oxy group and the reactive functional group and is not particularly limited as far as it does not contain a sulfide bond and is a group capable of forming a covalent bond between both groups but preferably includes groups having 1 to 8 carbon atoms, preferably 1 to 6 carbon atoms, such as an alkylene group, a phenylene group, and an alkylene group containing an ester bond, a urethane bond, an amide bond, an ether bond, a carbonate bond, or a secondary amino group. Preferable alkylene group includes a methylene group, an ethylene group, a trimethylene group, a propylene group, an isopropylene group, a tetramethylene group, a butylene group, an isobutylene group, a pentamethylene group, a hexamethylene group, and the like. More preferably, a structure such as the following (z1) may be mentioned. As an alkylene group containing an ester bond, further preferably, a structure such as the following (z2) may be mentioned. As an alkylene group containing an amide bond, more preferably, a structure of the following (z3) may be mentioned. As an alkylene group containing an ether bond, more preferably, a structure of the following (z4) may be mentioned. As an alkylene group containing a urethane bond, further preferably, a structure of the following (z5) may be mentioned. As an alkylene group containing a secondary amino group, more preferably, a structure of the following (z6) may be mentioned. In each formula, s is an integer of 1 to 6, preferably an integer of 1 to 3, further preferably an integer of 2 to 3.

Group (II)

[Chem 6]

—(CH₂)ₛ—     (z1)

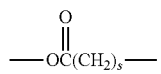
    (z2)

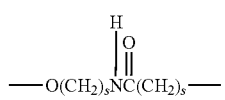
    (z3)

—O(CH₂)ₛ—     (z4)

    (z5)

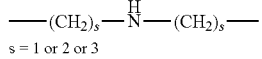
    (z6)

s = 1 or 2 or 3 wherein s is an integer of 1 to 6, preferably 1, 2, or 3.

$R^1$ is a hydrocarbon group having 1 to 10 carbon atoms which may contain fluorine atoms and specific hydrocarbon groups include hydrocarbon groups such as a methyl group, an ethyl group, a propyl group, an isopropyl group, a butyl group, a tert-butyl group, a hexyl group, a nonyl group, a vinyl group, a phenyl group, a benzyl group, a 4-methylphenyl group, a trifluoromethyl group, a 2,2,2-trifluoromethyl group, a 4-(trifluoromethoxy)phenyl group, and the like. Preferred are a methyl group, a vinyl group, a 4-methylphenyl group, and a 2,2,2-trifluoromethyl group.

$W^1$ represents a halogen atom such as Cl or Br, preferably Br or I, more preferably I.

In the specification, R is a hydrogen atom or a hydrocarbon group having 1 to 20 carbon atoms and specific hydrocarbon groups include alkyl groups (in the formula, to 7 carbon atoms) such as a methyl group, an ethyl group, a propyl group, an isopropyl group, a butyl group, a tert-butyl group, a pentyl group, an isopentyl group, a hexyl group, and a heptyl group, aralkyl groups such as a benzyl group, a cresyl group, a butylphenyl group, and a trityl group, and the like. The hydrocarbon group is preferably a hydrocarbon group having 1 to 7 carbon atoms, more preferably a hydrocarbon group having 1 to 4 carbon atoms such as a methyl group, an ethyl group, or a tert-butyl group or a benzyl group, further preferably a methyl group.

The "bio-related substance" according to the invention means a substance relating to a living body and examples thereof include a substance constituting a living body or a substance having physiological activity toward a living body (physiologically active substance). The bio-related substance capable of being modified with the multibranched polyoxyalkylene derivative of the formula (1) include the following, for example.

(1) Animal Cell-Constituting Materials Such as Phospholipids, Glycolipides, and Glycoproteins The animal cell-constituting materials are components constituting cell membranes or the like and the kind is not particularly limited but examples thereof include phospholipids, glycolipides, and glycoproteins. Examples of more specific phospholipids include phosphatidic acid, phosphatidylcholine, phosphatidylethanolamine, cardiolipin, phosphatidylserine, and phosphatidylinositol. In addition, lyso isomers thereof are also included. These phospholipids may be those derived from natural products such as egg yolk or soybean or may be synthesized products. The composition of fatty acids is not particularly limited but may preferably include fatty acids having 12 to 22 carbon atoms. These fatty acids may be saturated fatty acids or may be those containing an unsaturated bond. Examples of more specific glycolipids include ceramides, cerebrosides, sphingosines, gangliosides, and glyceroglycolipids. In addition, fatty acids, monoglycerides, diglycerides, cholesterols, and bile acid are also included.

(2) Body Fluid-Constituting Substances Such as Blood, Lymph, and Bone Marrow Liquid The body fluid-constituting substances mean fluid components existing inside and outside cells and the kind is not particularly limited but examples thereof include blood, lymph, and bone marrow liquid. Examples of more specific components constituting these body fluids include hemoglobin, albumin, blood coagulation factors, and the like.

(3) Physiologically Active Substances Such as Vitamins, Neurotransmitters, Proteins, Polypeptides, and Drugs The physiologically active substances mean components controlling body functions and the kind is not particularly limited but examples thereof include vitamins, neurotransmitters, proteins, polypeptides, and drugs.

Examples of more specific vitamins include vitamin A, vitamin B, vitamin C, vitamin D, vitamin E, vitamin K, and the like.

Examples of more specific neurotransmitters include adrenalin, noradrenalin, dopamine, acetylcholine, GABA, glutamic acid, aspartic acid, and the like.

Examples of more specific proteins and polypeptides include the following. Hormones such as neurohypophysial hormone, thyroid hormone, male sex hormone, female sex hormone, and adrenal cortex hormone. Serum proteins such as hemoglobin and blood factors. Immunoglobulins such as IgG, IgE, IgM, IgA, and IgD. Cytokines and fragments thereof, such as interleukins (IL-1, IL-2, IL-3, IL-4, IL-5, IL-6, IL-7, IL-8, IL-9, IL-10, IL-11 and IL-12 subtypes), interferons (-α, -β, -γ), granulocyte-colony stimulating factors (α and β types), macrophage-colony stimulating factor, granulocyte-macrophage colony stimulating factor, platelet-derived growth factor, phospholipase-activating protein, insulin, glucagon, lectin, ricin, tumor necrosis factor, epidermal growth factor, transforming growth factors (-α, -β), fibroblast growth factor, hepatocyte growth factor, vascular endothelial growth factor, nerve growth factor, bone growth factor, insulin-like growth factor, heparin binding growth factor, tumor growth factor, glial cell line-derived neurotrophic factor, macrophage differentiating factor, differentiation-inducing factor, leukemia inhibitory factor, amphiregulin, somatomedin, erythropoietin, hemopoietin, thrombopoietin, and calcitonin. Enzymes such as proteolytic enzymes, oxidoreductases, transferases, hydrolases, lyases, isomerases, ligases, asparaginases, arginases, arginine deaminases, adenosine deaminases, superoxide dismutases, endotoxinases, catalases, chymotrypsin, lipases, uricases, elastases, streptokinases, urokinases, prourokinases, adenosine diphosphatases, tyrosinases, bilirubin oxidases, glucose oxidases, glucodases, galactosidases, glucocerebrosidases, and glucuronidases. Monoclonal and polyclonal antibodies and fragments thereof. Polyamino acids such as poly-L-lysine and poly-D-lysine. Vaccines such as hepatitis B vaccine, malaria vaccine, melanoma vaccine, and HIV-1 vaccine, and antigens. In addition, glycoproteins are also included. Furthermore, also included are structurally similar substances having physiological activity similar to that of these physiologically active substances.

Moreover, these proteins and polypeptides may be isolated from natural sources thereof or cells subjected to genetic engineering or may be produced via various synthetic processes.

The drugs, i.e., physiologically active substances are not particularly limited but more preferably include anticancer agents and antifungal agents.

More specific anticancer agents are not particularly limited but, for example, include paclitaxel, adriamycin, doxorubicin, cisplatin, daunomycin, mitomycin, vincristine, epirubicin, methotrexate, 5-fluorouracil, aclacinomycin, idamycin, bleomycin, pirarubicin, peplomycin, vancomycin, and camptothecine.

Specific antifungal agents are not particularly limited but, for example, include amphotericin B, nystatin, flucytosine, miconazole, fluconazole, itraconazole, ketoconazole, and peptide antifungal agents.

Moreover, these physiologically active substances also include flavonoids, terpenoids, carotenoids, saponins, steroids, quinones, anthraquinones, xanthones, coumarins, alkaloids, porphyrins, and polyphenols, which possess, for example, antioxidant action, PAF inhibitory action, antiinflammatory action, and antifungal action.

The multibranched polyoxyalkylene derivative (1A) can be produced by converting the following compound (p1a), which is a polyoxyalkylene derivative, into a compound having a functional group reactive with a bio-related substance.

[Chem 7]

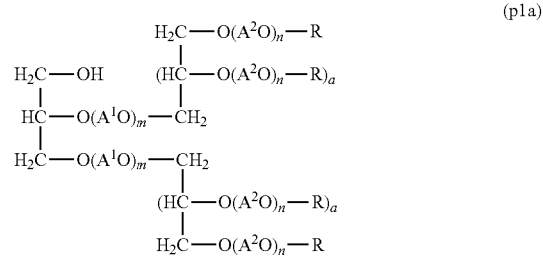

(p1a)

Moreover, the compound (p1a) can be produced by the route, for example, shown in the following scheme.

[Chem 8]

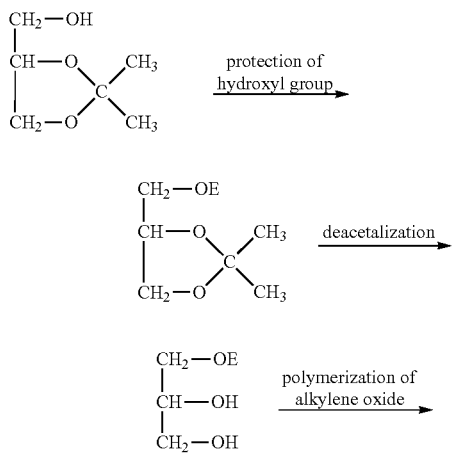

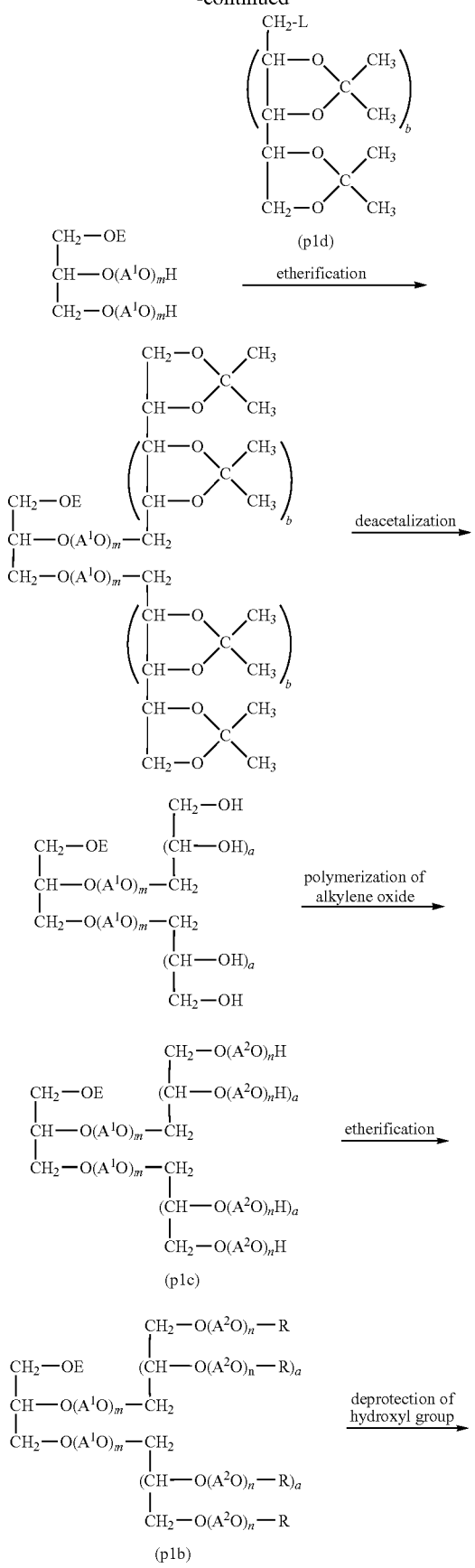

(p1d)

(p1c)

(p1b)

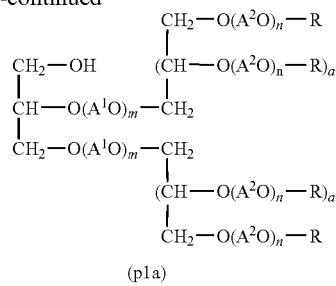

(p1a)

wherein E represents a protective group of a hydroxyl group, L represents a leaving group, and the other symbols have the same meanings as above.

As the protective group of a hydroxyl group, a benzyl group, a t-butyl group, a trityl group, or the like may be mentioned. As the leaving group, a sodium oxide group, a potassium oxide group, a halogen group such as Cl or Br, a mesyl group, a tresyl group, or the like may be mentioned.

In the above scheme, an intermediate including the formulae (p1a), (p1b), and (p1c) corresponds to the polyoxyalkylene derivative (1B).

A suitable specific example of the production of the compound (p1a) will be described below.

After the hydroxyl group of 2,2-dimethyl-1,3-dioxolan-4-methanol is protected with a protective group (e.g., a benzyl group or a t-butyl group), the cyclic acetal structure is cleaved under an acidic condition to produce two hydroxyl groups. To the two hydroxyl groups, an alkylene oxide is usually polymerized in an amount of 40 to 1000 mol.

[Chem 9]

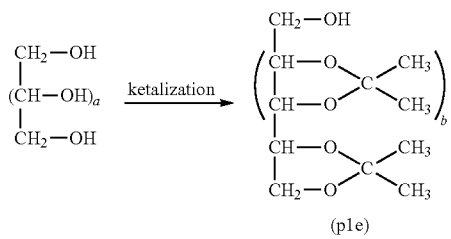

(p1e)

In order to obtain a polyhydric alcohol derivative (p1e) wherein b is 0, 1, or 2, using a polyhydric alcohol wherein a is 1, 3 or 5, respectively, ketalization can be carried out using general protection methods of a hydroxyl group as described in, for example, PROTECTIVE GROUPS IN ORGANIC SYNTHESIS (THEODORA W. GREENE at al.).

Such ketalization may include one carried out on the adjacent or non-adjacent hydroxyl groups. Moreover, as (p1e), any of isomers produced by these methods may be used.

A compound (p1d) obtained by introducing a leaving group L into the resulting polyhydric alcohol derivative (p1e) is bonded to a terminal end of a polyoxyalkylene and then the cyclic acetal structure is cleaved to produce four hydroxyl group in the case of a is 1, i.e., b is 0, eight hydroxyl groups in the case of a is 3, i.e., b is 1, and twelve hydroxyl groups in the case of a is 5, i.e., b is 2. The cleavage is usually carried out under an acidic condition. To a plurality of the hydroxyl groups, an alkylene oxide is polymerized usually in an amount of 50 to 2000 mol and then the terminal end is alkyl-etherified. Then, the protective group E is cleaved to produce a new hydroxyl group (the above compound (p1a)).

[Chem 10]

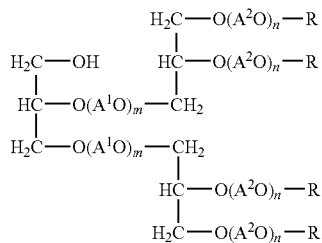

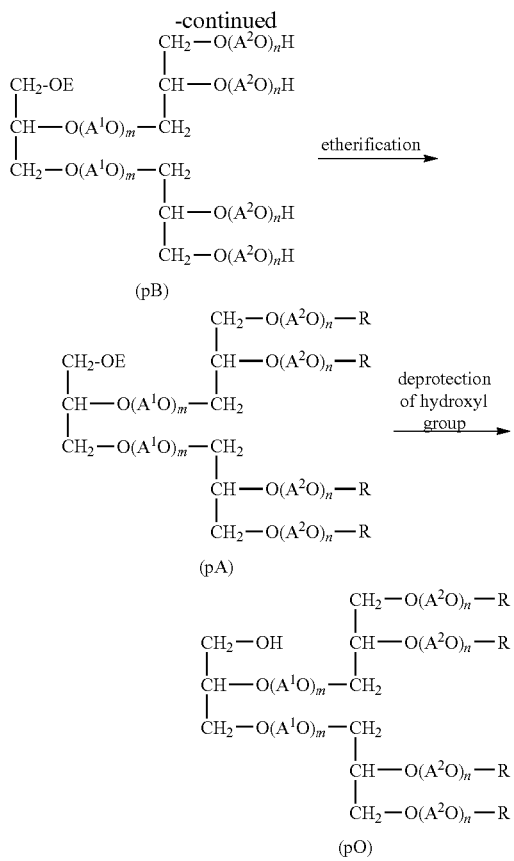

Hereinafter, since the same production method is applicable to any of the cases where a is 1, 3, or 5, i.e., b is 0, 1, 2, the case where a is 1, i.e., b is 0 will be described.

The compound (p0) where a is 1, i.e., b is 0 can be produced by the route shown in the following scheme.

[Chem 11]

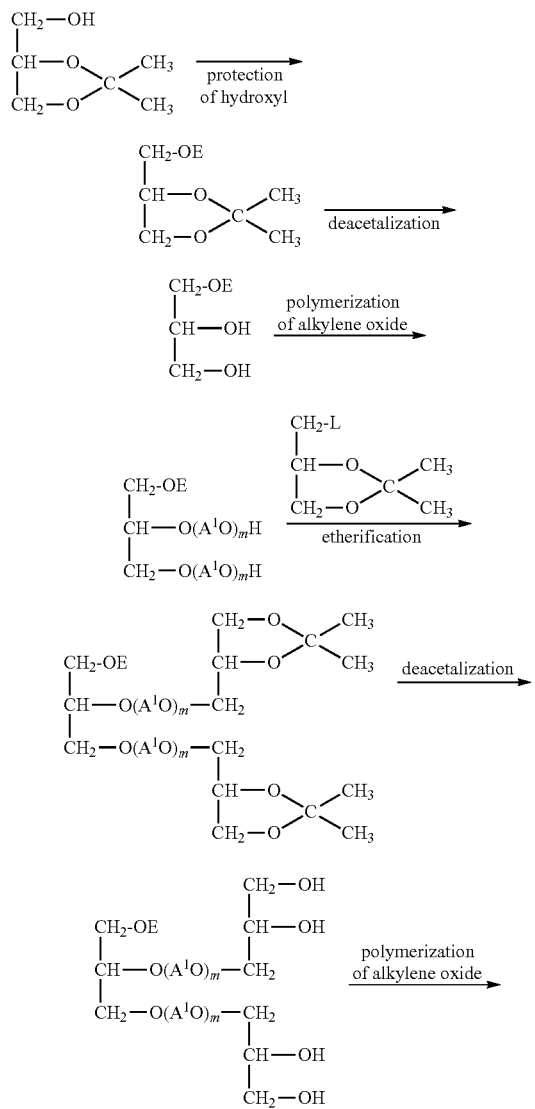

wherein E represents a protective group of a hydroxyl group, L represents a leaving group, and the other symbols have the same meanings as above.

As the protective group E of a hydroxyl group, a benzyl group, a t-butyl group, a trityl group, or the like may be mentioned. As the leaving group L, a sodium oxide group, a potassium oxide group, a halogen group such as Cl or Br, a mesyl group, a tresyl group, or the like may be mentioned.

In the above scheme, an intermediate including the formulae (p0), (pA), and (pB) corresponds to the polyoxyalkylene derivative (A).

A suitable specific example of the production of the compound (p0) will be described below.

After the hydroxyl group of 2,2-dimethyl-1,3-dioxolan-4-methanol is protected with a protective group (e.g., a benzyl group or a t-butyl group), the cyclic acetal structure is cleaved under an acidic condition to produce two hydroxyl groups. To the two hydroxyl groups, an alkylene oxide is usually polymerized in an amount of 40 to 1000 mol. Furthermore, after 2,2-dimethyl-1,3-dioxolane-4-methanol is bonded to the terminal end, the cyclic acetal structure is cleaved to produce four hydroxyl groups. The cleavage is usually performed under an acidic condition. To the four hydroxyl groups, an alkylene oxide is polymerized usually in an amount of 50 to 2000 mol and then the terminal ends are alkyl-etherified. Then, the protective group such as a benzyl group or a t-butyl group is cleaved to produce a new hydroxyl group (the above compound (p0)).

In the case of the compound where R is a hydrogen atom, at the terminal alkyl-etherification, after the etherification with a protective group which is different from the protective group with which the hydroxyl group of 2,2-dimethyl-1,3-dioxolane-4-methanol is protected, the protective group with which the hydroxyl group of 2,2-dimethyl-1,3-dioxolane-4-methanol is protected is cleaved to produce a new hydroxyl group. After the hydroxyl group is converted to a functional group by the method to be mentioned below, the protective group of the terminal hydroxyl group of the polyoxyalkylene chain is cleaved to obtain the target compound.

As above, a highly pure poly(alkylene glycol) derivative can be produced in high yields in an industrially suitable manner by using the alkylene oxide-addition polymerization reaction, without column purification.

As the protection with a protective group, e.g., benzyl-etherification of the hydroxyl group of 2,2-dimethyl-1,3-dioxolane-4-methanol, the following methods may be mentioned.

1) It can be achieved by reacting benzyl chloride or benzyl bromide with 2,2-dimethyl-1,3-dioxolane-4-methanol in an aprotic solvent or without any solvent in the presence of an alkali catalyst such as sodium hydroxide or potassium hydroxide.

2) It can be achieved by converting the hydroxyl group of 2,2-dimethyl-1,3-dioxolane-4-methanol in an aprotic solvent or without any solvent using metallic sodium, metallic potassium, sodium hydride, potassium hydride, sodium methoxide, potassium methoxide, potassium t-butoxide, or the like into an alcoholate and reacting the alcoholate with benzyl chloride or benzyl bromide under a basic condition.

3) It can be achieved by activating the hydroxyl group of 2,2-dimethyl-1,3-dioxolane-4-methanol with methanesulfonyl chloride, p-toluenesulfonyl chloride, 2,2,2-trifluoroethanesulfonyl chloride, or the like in an aprotic solvent or without any solvent, followed by the reaction with an alcoholate of benzyl alcohol.

The deprotection of the cyclic acetal structure which follows the benzyl etherification is achieved by the reaction in an aqueous solution adjusted to pH 1 to 4 with an acid such as acetic acid, phosphoric acid, sulfuric acid, or hydrochloric acid, whereby a compound of the formula (7) can be produced.

The method of addition polymerization of an alkylene oxide to the compound of the formula (7) having two hydroxyl groups newly formed by the deprotection of the cyclic acetal structure is not particularly limited but can be achieved via the following steps (D1) and (D2).

[Chem 12]

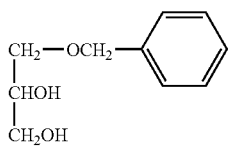

(7)

Step (D1): as a method of alcoholation of the compound of the formula (7), the alcoholation is carried out using metallic sodium or potassium, preferably metallic sodium as a catalyst, in an catalyst amount of 5 to 50% by mol, followed by dissolution at 10 to 50° C.

Step (D2): alkylene oxide addition polymerization is carried out at a reaction temperature of 50 to 130° C.

With regard to the catalyst amount in the step (D1), since the polymerization rate of the alkylene oxide decreases at less than 5% by mol and heat history increases to result in the formation of impurities such as a terminal vinyl ether compound, the use of the catalyst in an amount of 5% by mol or more is advantageous in the production of a high quality high-molecular-weight compound. When the catalyst amount exceeds 50% by mol, the viscosity of the reaction solution increases or the solution solidifies at the alcoholation reaction and thus there is a tendency that the stirring efficiency decreases and the alcoholation is not accelerated. Moreover, when the solution solidifies, handling thereof tends to be difficult, which causes water absorption. When the alcoholate has absorbed water, an alkylene glycol compound derived from water is formed and is contained as an impurity undesirable in medical use.

When the temperature at the dissolution is higher than 50° C., a decomposition reaction may occur to form benzyl alcohol and glycerin. When benzyl alcohol is formed, it initiates addition polymerization with the alkylene oxide, whereby a low-molecular-weight impurity having a molecular weight 0.5 time the molecular weight of the target compound. When the low-molecular-weight impurity derived from benzyl alcohol is formed, a functional group is introduced via alkyl-etherification of the hydroxyl group and deprotection in the subsequent steps as in the case of the target compound, so that the impurity is converted into a low-molecular-weight impurity which is reactive with a bio-related substance. There is a possibility that such an impurity may react with a bio-related substance and change the properties of the resulting preparation. Moreover, when glycerin is formed, it also initiates addition polymerization with the alkylene oxide to form a high-molecular-weight impurity having a molecular weight 1.5 times that of the target compound. Since the high-molecular-weight impurity does not have a benzyl group and its terminal hydroxyl group is only alkyl-etherified, no functional group is introduced. However, when the combination with a drug or the like is carried out while such an impurity is contained, the resulting preparation becomes inhomogeneous and hence the quality tends to be varied. Also, the preparation is not suitable in a medical use where a highly pure product is required.

When the dissolution is carried out at a temperature lower than 10° C., like the case where the catalyst amount is more than 50% by mol, the viscosity of the reaction solution increases or the solution solidified at the alcoholation reaction, and handling thereof tends to be difficult, and water absorption is caused.

The reaction solvent is not particularly limited as far as it is an aprotic solvent such as toluene, benzene, xylene, acetonitrile, ethyl acetate, tetrahydrofuran, chloroform, methylene dichloride, dimethyl sulfoxide, dimethylformamide, or dimethylacetamide, but preferable is toluene or no solvent. The reaction time is preferably 1 to 24 hours. When the time is shorter than 1 hour, there is a concern that the catalyst does not completely dissolved. When the time is longer than 24 hours, there is a concern that the above decomposition reaction may occur.

With regard to the reaction temperature in the step (D2), when the temperature is lower than 50° C., the polymerization rate is low and heat history increases to result in a tendency to decrease the quality of the compound of the formula (6). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction solution also increases, so that an aprotic solvent, preferably toluene may be optionally added.

As another production process in the step of alcoholation, the following step (D3) may be mentioned.

Step (D3): Sodium methoxide, potassium t-butoxide, or potassium methoxide, preferably sodium methoxide is added as an catalyst in an amount of 5 to 50% by mol and the reaction is carried out at 60 to 80° C. At that time, a pressure-reducing operation may be conducted in order to facilitate the exchange reaction.

The catalyst amount is preferably 5 to 50% by mol for the reason mentioned above. With regard to the reaction temperature, when the temperature is lower than 60° C., the conversion of the exchange reaction decreases and alcohols such as methanol remain, which leads to the formation of impurities having a molecular weight 0.5 time that of the target compound via addition polymerization of an alkylene oxide. When the temperature is higher than 80° C., a decomposition reaction occurs. The alcoholation reaction requires elevation of the temperature and the reaction time is desirably 1 to 3 hours since the decomposition reaction is apt to occur. When the time is shorter than 1 hour, there is a concern that the conversion into the alcoholate decreases. When the time is longer than 3 hours, a decomposition reaction may occur. The reaction solvent is not particularly limited as far as it is an aprotic solvent, but preferable is toluene or no solvent.

The subsequent etherification of the terminal end with 2,2-dimethyl-1,3-dioxolan-4-methanol (IPG formation) may be achieved by either of the following (1) or (2):

(1) a process of converting the terminal end of the poly(alkylene glycol) chain into an alcoholate and reacting it with mesylated 2,2-dimethyl-1,3-dioxolan-4-methanol (2,2-dimethyl-1,3-dioxolan-4-methyl methanesulfonate);

(2) a process of activating the terminal hydroxyl group of the poly(alkylene glycol) chain with methanesulfonyl chloride, p-toluenesulfonyl chloride, 2,2,2-trifluoroethanesulfonyl chloride, or the like, followed by the reaction with an alcoholate of 2,2-dimethyl-1,3-dioxolan-4-methanol.

Preferable is the process (2) and the following will describe it in more detail.

The production process (2) comprises the following steps (C1), (C2), and (C3).

Step (C1): a step of adding a dehalogenating agent and a compound represented by the formula (6a) to a compound represented by the formula (6) and reacting them at 20 to 60° C. to obtain a compound of the formula (5).

[Chem 13]

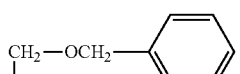

(6)

[Chem 14]

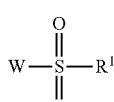

(6a)

[Chem 15]

-continued

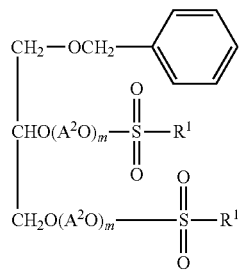

(5)

The dehalogenating agent to be used includes organic bases such as triethylamine, pyridine, and 4-dimethylaminopyridine, and inorganic bases such as sodium carbonate, sodium hydroxide, sodium hydrogen carbonate, sodium acetate, potassium carbonate, and potassium hydroxide. Preferable dehydrochlorinating agent is an organic base such as triethylamine, pyridine, or 4-dimethylaminopyridine. Moreover, the amount of the dehalogenating agent to be used in the reaction is preferably 1 to 8 equivalents, more preferably 1 to 4 equivalents to one hydroxyl group in the formula (6).

In the compound of the formula (6a) to be used, W is a group reactive with a hydroxyl group, preferably Cl or Br, and $R^1$ is a hydrocarbon group having 1 to 10 carbon atoms, which may contain a fluorine atom, preferably a methyl group, a phenyl group, or a p-methylphenyl group. More suitably, methanesulfonyl chloride where W is Cl and $R^1$ is a methyl group is most preferable. Moreover, the amount of the compound (6a) to be used in the reaction is preferably 1 to 6 equivalents, more preferably 1 to 3 equivalents to one hydroxyl group in the formula (6).

The solvent to be used at that time is not particularly limited as far as it is an aprotic solvent and preferably includes toluene, benzene, xylene, acetonitrile, ethyl acetate, tetrahydrofuran, chloroform, methylene dichloride, dimethyl sulfoxide, dimethylformamide, or dimethylacetamide, but more preferable is toluene which enables azeotropic removal of water in the system. The amount of the solvent to be used at the reaction is preferably 0.5 equivalent weight to 10 equivalent weight to the compound of the formula (6). In the case where the compound of the formula (6) has a large molecular weight, the viscosity of the reaction solution increases and the conversion decreases, so that it is preferable to dilute the reaction solution with the solvent.

The reaction temperature is not particularly limited but is preferably 60° C. or lower for the purpose of suppressing side reactions and is preferably 20° C. or higher for the purpose of inhibiting increase of the viscosity of the reaction solution. The reaction time is preferably 1 to 24 hours. When the time is shorter than 1 hour, there is a concern that the conversion is low. When the time is longer than 24 hours, there is a concern that a side reaction may occur.

At the reaction, the operation of removing water from the starting materials, such as azeotropic removal of water may be carried out prior to the reaction. Moreover, an antioxidant such as 2,6-di-tert-butyl-p-cresol may be added. Furthermore, a salt is formed with the progress of the reaction and the formation of the compound of the formula (5), but the reaction mixture may be used in the subsequent step as it is, or the salt may be removed by filtration, or after the filtration, the compound of the formula (5) may be purified by a purification means such as extraction, recrystallization, adsorption treatment, reprecipitation, column chromatography, or supercritical extraction.

Step (C2): a step of adding a compound represented by the formula (7a) to the compound of the formula (5) and reacting them at 20 to 80° C. to obtain the compound of the formula (4).

[Chem 16]

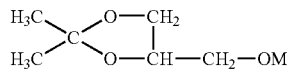
(7a)

In the formula (7a), M is an alkali metal such as sodium or potassium, preferably sodium.

The amount of the compound (7a) to be used in the reaction is preferably 2 to 8 equivalents, more preferably 2 to 5 equivalents to one functional group derived from the compound (6a) of the formula (5).

The solvent to be used in the reaction is not particularly limited as far as it is an aprotic solvent as mentioned above and is preferably toluene. The amount of the solvent to be used at the reaction is preferably an amount of 0.5 equivalent to 10 equivalents to the compound of the formula (5). In the case where the compound of the formula (5) has a large molecular weight, the viscosity of the reaction solution increases, so that it is preferable to dilute the reaction solution with the solvent.

The reaction temperature is not particularly limited but is preferably 80° C. or lower for the purpose of suppressing side reactions and is preferably 20° C. or higher for the purpose of inhibiting increase of the viscosity of the reaction solution. The reaction time is preferably 1 to 24 hours. When the time is shorter than 1 hour, there is a concern that the conversion is low. When the time is longer than 24 hours, there is a concern that a side reaction occurs. At the reaction, an operation of removing water from the starting materials, such as azeotropic removal of water may be carried out prior to the reaction.

Step (C3): a step of filtrating the reaction solution or washing the reaction solution with an aqueous inorganic salt solution having a concentration of 10% by weight or more.

In the step, the inorganic salt is not particularly limited but is preferably sodium chloride. When the concentration is less than 10% by weight, the target compound migrates into an aqueous layer to decrease the process yield. The operation of washing with water may be repeated several times. The step (C3) is carried out for removing starting materials excessively added and salts produced as by-products. The omission of the step may cause side reactions in the case where the steps (C1) to (C3) are again carried out in the next place.

Moreover, in order to enhance the ratio of IPG formation of the oxyalkylene chain terminal end, it is preferable to repeat the steps (C1) to (C3) again. When the ratio of IPG formation of the oxyalkylene chain terminal end is low, as mentioned above, there is a concern that a polyfunctional impurity may be formed.

The compound of the formula (4) thus obtained may be purified by a purification means such as extraction, recrystallization, adsorption treatment, reprecipitation, column chromatography, or supercritical extraction.

[Chem 17]

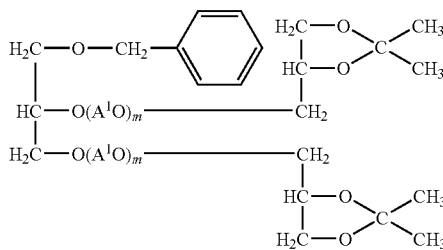
(4)

The deprotection of the cyclic acetal structure of the compound of the formula (4) is carried out by the conversion into an aqueous solution adjusted to pH 1 to 4 with an acid such as acetic acid, phosphoric acid, sulfuric acid, or hydrochloric acid, whereby the compound of the formula (3) can be produced.

[Chem 18]

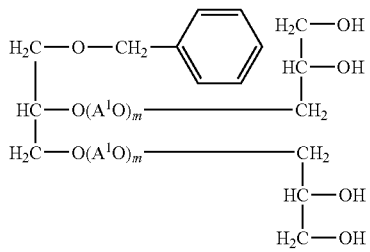
(3)

The production of the compound of the formula (2) by addition polymerization of an alkylene oxide to the formula (3) having four hydroxyl groups newly formed by the deprotection of the cyclic acetal structure is not particularly limited but the compound can be produced via the following steps (B1) and (B2).

Step (B1): as a method of alcoholation of the compound of the formula (3), an exchange reaction is carried out using sodium methoxide, potassium t-butoxide, or potassium methoxide, preferably sodium methoxide as a catalyst, with adding it in an catalyst amount of 2 to 25% by mol to the formed hydroxyl group at 60 to 100° C., without any solvent or after the compound is dissolved in a solvent such as toluene and water removal is performed under reflux, and removing methanol contained at 60 to 100° C. under a vacuum of 0.05 to 0 MPa over a period of 0.2 to 4 hours. Additionally, toluene contained is removed at 60 to 130° C. under a vacuum of 0.05 to 0 MPa.

Step (B2): an alkylene oxide addition polymerization is carried out at a reaction temperature of 50 to 130° C.

With regard to the catalyst amount in the step (B1), since the polymerization rate of the alkylene oxide decreases at less than 2% by mol and heat history increases to result in the formation of impurities such as a terminal vinyl ether compound, the use of the catalyst in an amount of 2% by mol or more is advantageous in the production of a high quality high-molecular-weight compound. When the catalyst amount exceeds 25% by mol, the viscosity of the reaction solution increases or the solution solidifies at the alcoholation reaction and thus there is a tendency that the stirring efficiency decreases and the alcoholation is not accelerated. Moreover, when the solution solidifies, handling thereof tends to be difficult, which causes water absorption. When the alcoholate has absorbed water, an alkylene glycol compound derived from water is formed and is contained as an impurity undesirable in medical use.

When the temperature at the exchange reaction is lower than 60° C., the conversion of the exchange reaction decreases and an alcohol such as methanol remains, so that impurities different from the target compound are formed via addition polymerization of the alkylene oxide. When the temperature is higher than 80° C., a decomposition reaction may occur. In the alcoholation reaction, it is necessary to raise the temperature but the exchange reaction time is desirably 0.2 to 4 hours since the decomposition reaction is apt to occur. When the time is shorter than 0.2 hour, there is a concern that the conversion of the alcoholation reaction decreases. When the time is longer than 4 hours, there is a concern that the decomposition reaction occurs.

At the removal of toluene, when the temperature is higher than 130° C., the decomposition reaction occurs, where elimination of a polyoxyalkylene chain occurs and a product having a half of the molecular weight is formed. When the temperature is lower than 60° C., there is a possibility of solidification, which may result in a problem of handling.

The reaction solvent is not particularly limited as far as it is an aprotic solvent such as toluene, benzene, xylene, acetonitrile, ethyl acetate, tetrahydrofuran, chloroform, methylene dichloride, dimethyl sulfoxide, dimethylformamide, or dimethylacetamide, but preferable is toluene or no solvent. The reaction time is preferably 1 to 24 hours. When the time is shorter than 1 hour, there is a concern that the catalyst does not completely dissolved. When the time is longer than 24 hours, there is a concern that the above decomposition reaction may occur.

With regard to the reaction temperature in the step (B2), when the temperature is lower than 50° C., the polymerization rate is low and heat history increases to result in a tendency to decrease the quality of the compound of the formula (2). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction solution also increases, so that an aprotic solvent, preferably toluene may be optionally added.

[Chem 19]

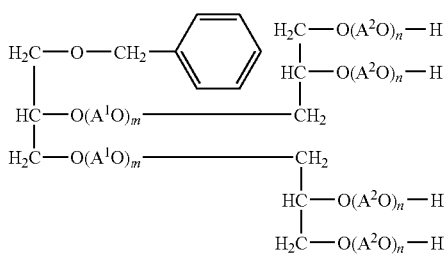

(2)

The subsequent alkyl-etherification of the terminal end may be achieved by either of the following (1) or (2):
(1) a process of converting the terminal end of the poly(alkylene glycol) chain into an alcoholate and reacting it with an alkyl halide;
(2) a process of activating the terminal hydroxyl group of the poly(alkylene glycol) chain with methanesulfonyl chloride, p-toluenesulfonyl chloride, 2,2,2-trifluoroethanesulfonyl chloride, or the like, followed by the reaction with an alcoholate of an alkyl alcohol.

Preferable is the process (2) and the following will describe it in more detail.

The production process (2) comprises the following steps (A1), (A2), and (A3).
Step (A1): a step of adding a dehalogenating agent and a compound represented by the formula (6a) to a compound represented by the formula (2) and reacting them at 20 to 60° C.

[Chem 20]

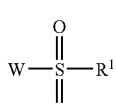

(6a)

[Chem 21]

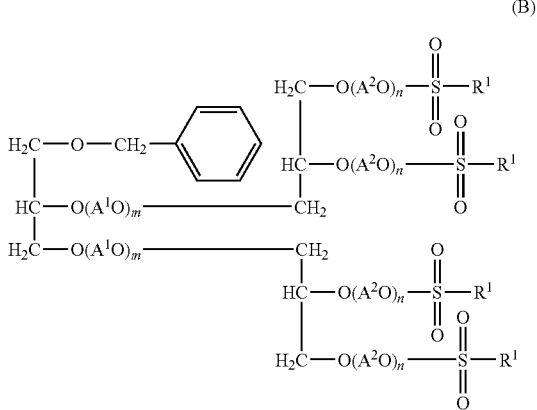

(B)

The dehalogenating agent to be used includes organic bases such as triethylamine, pyridine, and 4-dimethylaminopyridine, and inorganic bases such as sodium carbonate, sodium hydroxide, sodium hydrogen carbonate, sodium acetate, potassium carbonate, and potassium hydroxide. Preferable dehydrochlorinating agent is an organic base such as triethylamine, pyridine, or 4-dimethylaminopyridine. Moreover, the amount of the dehalogenating agent to be used in the reaction is preferably 1 to 8 equivalents, more preferably 1 to 4 equivalents to one hydroxyl group in the formula (2).

In the compound of the formula (6a) to be used, W is preferably Cl or Br, and $R^1$ is preferably a methyl group, a phenyl group, or a p-methylphenyl group. More suitably, methanesulfonyl chloride where W is Cl and $R^1$ is a methyl group is most preferable. Moreover, the amount of the compound (6a) to be used in the reaction is preferably 1 to 6 equivalents, more preferably 1 to 3 equivalents to one hydroxyl group in the formula (2).

The solvent to be used at that time is not particularly limited as far as it is an aprotic solvent and preferably includes toluene, benzene, xylene, acetonitrile, ethyl acetate, tetrahydrofuran, chloroform, methylene dichloride, dimethyl sulfoxide, dimethylformamide, or dimethylacetamide, but more preferable is toluene which enables azeotropic removal of water in the system. The amount of the solvent to be used at the reaction is preferably 0.5 equivalent weight to 10 equivalent weight to the compound of the formula (2). In the case where the compound of the formula (2) has a large molecular weight, the viscosity of the reaction solution increases and the conversion decreases, so that it is preferable to dilute the reaction solution with the solvent.

The reaction temperature is not particularly limited but is preferably 60° C. or lower for the purpose of suppressing side reactions and is preferably 20° C. or higher for the purpose of inhibiting increase of the viscosity of the reaction solution. The reaction time is preferably 1 to 24 hours. When the time is shorter than 1 hour, there is a concern that the conversion is low. When the time is longer than 24 hours, there is a concern that a side reaction may occur.

At the reaction, the operation of removing water from the starting materials, such as azeotropic removal of water may be carried out prior to the reaction. Moreover, an antioxidant such as 2,6-di-tert-butyl-p-cresol may be added. Furthermore, a salt is formed with the progress of the reaction and the formation of the compound of the formula (B), but the reaction mixture may be used in the subsequent step as it is, or the salt may be removed by filtration, or after the filtration, the compound of the formula (B) may be purified by a purification means such as extraction, recrystallization, adsorption treatment, reprecipitation, column chromatography, or supercritical extraction.

Step (A2): a step of adding a compound represented by the formula (1a) to the compound of the formula (B) and reacting them at 20 to 80° C. to obtain the compound of the formula (0).

[Chem 22]

R-OM (1a)

In the formula (1a), R is as mentioned above and M is an alkali metal such as sodium or potassium, preferably sodium.

The amount of the compound (1a) to be used in the reaction is preferably 2 to 8 equivalents, more preferably 2 to 5 equivalents to one hydroxyl group derived from the compound (6a) of the formula (B).

The solvent to be used in the reaction is not particularly limited as far as it is an aprotic solvent as mentioned above and is preferably toluene. The amount of the solvent to be used at the reaction is preferably an amount of 0.5 equivalent to 10 equivalents to the compound of the formula (B). In the case where the compound of the formula (B) has a large molecular weight, the viscosity of the reaction solution increases, so that it is preferable to dilute the reaction solution with the solvent.

The reaction temperature is not particularly limited but is preferably 80° C. or lower for the purpose of suppressing side reactions and is preferably 20° C. or higher for the purpose of inhibiting increase of the viscosity of the reaction solution. The reaction time is preferably 1 to 24 hours. When the time is shorter than 1 hour, there is a concern that the conversion is low. When the time is longer than 24 hours, there is a concern that a side reaction occurs. At the reaction, an operation of removing water from the starting materials, such as azeotropic removal of water may be carried out prior to the reaction.

Step (A3): a step of filtrating the reaction solution or washing the reaction solution with an aqueous inorganic salt solution having a concentration of 10% by weight or more.

In the step, the inorganic salt is not particularly limited but is preferably sodium chloride. When the concentration is less than 10% by weight, the target compound migrates into an aqueous layer to decrease the process yield remarkably. The operation of washing with water may be repeated several times. The step (A3) is carried out for removing starting materials excessively added and salts produced as by-products. The omission of the step may cause side reactions in the case where the steps (A1) to (A3) are again carried out in the next place. In the case where a debenzylation step is carried out as a next step, these impurities act as catalyst poisons and thus the conversion may be affected.

Moreover, in order to enhance the ratio of alkyl-etherification of the oxyalkylene chain terminal end, it is preferable to repeat the steps (A1) to (A3) again. When the ratio of alkyl-etherification of the oxyalkylene chain terminal end is low, as mentioned above, there is a concern that a polyfunctional impurity may be formed.

The compound of the formula (0) thus obtained may be purified by a purification means such as extraction, recrystallization, adsorption treatment, reprecipitation, column chromatography, or supercritical extraction.

[Chem 23]

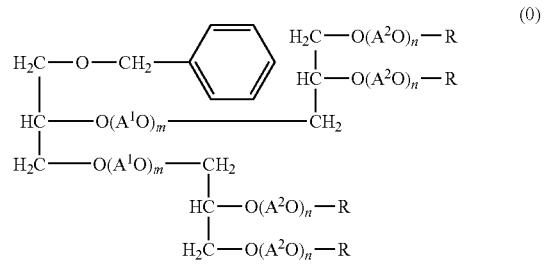

The production of the compound (p0) by successive debenzylation is not particularly limited but it can be produced by hydrogenation in the following step (Z) using a hydrogenative reduction catalyst and a hydrogen donor.

Step (Z): a step of subjecting the compound represented by the formula (0) to a hydrogenative reduction reaction.

The hydrogenative reduction catalyst is desirably a metal catalyst or the like, preferably nickel, palladium, particularly palladium. The support is not particularly limited but is preferably alumina or carbon, more preferably carbon. The amount of palladium is preferably 1 to 20% by weight based on the compound of the formula (0). When the amount is less than 1% by weight, the conversion of deprotection decreases and thus there is a concern that the ratio of functionalization in the next step decreases. Moreover, when the amount is more than 20% by weight, the decomposition reaction of the poly(alkylene glycol) chain may occur and there is a concern that the afore-mentioned reactive low-molecular-weight compound is produced as a by-product. The reaction solvent is not particularly limited but preferably includes methanol, ethanol, 2-propanol, and the like and more preferable is methanol. The hydrogen donor is not particularly limited but include hydrogen gas, cyclohexene, 2-propanol, ammonium formate, and the like. The reaction temperature is preferably 60° C. or lower. When the temperature is higher than 60° C., the decomposition reaction of the poly(alkylene glycol) chain may occur and there is a concern that a reactive low-molecular-weight compound is produced. The reaction time is not particularly limited. When large amount of the catalyst is used, the reaction is completed within a short period of time. But, when the amount is small, a longer period of time is required. The reaction time is preferably 1 to 5 hours. When the time is shorter than 1 hour, there is a concern that the conversion is low. When it is longer than 5 hours, the decomposition reaction of the poly(alkylene glycol) chain may occur.

The resulting compound of the formula (p0) may be purified by a purification means such as extraction, recrystallization, adsorption treatment, reprecipitation, column chromatography, or supercritical extraction.

The thus obtained compound is a poly(alkylene glycol) derivative represented by the following formula (p0) and containing substantially no secondary hydroxyl group:

[Chem 24]

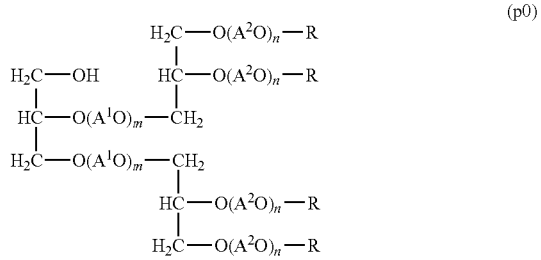

(p0)

wherein $A^1O$ and $A^2O$ represent an oxyalkylene group having 2 to 4 carbon atoms, m represents 20 to 500, n represents 15 to 700, and R represents a hydrogen atom or a hydrocarbon group having 1 to 20 carbon atoms.

Since the compound of the formula (p0) contains substantially no secondary hydroxyl group, the conversion of the subsequent functional group-introducing reaction is high and a highly pure poly(alkylene glycol) derivative can be obtained. In the case where a secondary hydroxyl group is present, the conversion of the subsequent functional group-introducing reaction is low and the purity of the modified bio-related substance decreases, so that there may arise the problem of contamination of the drug or the like with an impurity.

The hydroxyl group of the compound (p0) can be converted into various functional groups by the following methods. For example, the production can be carried out by the production methods described in Laboratory Synthesis of Polyethylene Glycol Derivatives (J. MILTON HARRIS et al), POLY(ETHYLENE GLYCOL) CHEMISTRY (J. MILTON HARRIS), JP-A-7-316285, and JP-T-2007-508427. Moreover, even in the case of the multibranched polyoxyalkylene derivative (1B), functional groups can be introduced by the similar methods.

(1) Introduction of Carboxyl Group with Halogenated Alkylcarboxylic Acid Derivative, Succinic Anhydride, Glutaric Anhydride, or the Like and Conversion into Active Ester Thereof The halogenated alkylcarboxylic acid derivative can be obtained as follows: for example, a branched polyoxyalkylene derivative having a hydroxyl group is dissolved in toluene, after removal of water at 110° C., potassium hydroxide is added at 40° C., and ethyl 6-bromohexanoate is reacted by adding dropwisely; after water is added to the reaction solution to perform hydrolysis, the reaction solution is made acidic with hydrochloric acid and, after removal of the toluene layer, is extracted with chloroform and concentrated, and crystallization was performed with ethyl acetate.

Moreover, a branched polyoxyalkylene derivative having a hydroxyl group is dissolved in toluene and, after removal of water at 110° C., sodium acetate, succinic anhydride, or glutaric anhydride is added to perform the reaction. After cooling, the reaction solution is filtrated, crystallization is performed with hexane and crystals are precipitated using ethyl acetate and hexane, whereby a polyoxyalkylene succinate or glutarate ester derivative can be obtained.

These carboxyl derivatives are dissolved in toluene, activated by adding N-hydroxysuccinimide, dicyclohexylcarbodiimide at 40° C. and, after filtration, crystals are precipitated using ethyl acetate and hexane, whereby active esterified derivatives can be obtained.

(2) Mesylation with Methanesulfonyl Chloride

A branched polyoxyalkylene derivative having a hydroxyl group is dissolved in toluene and, after removal of water at 110° C., triethylamine and methanesulfonic acid are added at 40° C., the reaction is completed by adding ethanol, and then the filtrated reaction solution is subjected to crystal precipitation with ethyl acetate and hexane. Thus, a mesylated derivative can be obtained.

(3) Conversion into Mercapto Group Using Thiourea, Dithiocarbonate Ester, or the Like The mesylated derivative obtained in (2) is dissolved in 2-propanol, thiurea is added, after the reaction at 40° C., an aqueous sodium hydroxide solution is added to perform hydrolysis at 80° C., after the reaction solution is made acidic with hydrochloric acid, extraction is performed with chloroform, and, after concentration, crystals are precipitated with ethanol and hexane. Thus, a mercapto derivative can be obtained.

(4) Introduction of Active Carbonate Ester Group with P-Nitrophenyl Chlorocarbonate, Disuccinimidyl Carbonate, Carbodiimidazole, or the Like With regard to a p-nitrophenyl carbonate ester derivative, a branched polyoxyalkylene derivative having a hydroxyl group is dissolved in toluene and, after removal of water at 110° C., triethylamine and p-nitrophenyl chloroformate is added to perform the reaction at 60° C., and the filtrated reaction solution is subjected to crystal precipitation with ethyl acetate and hexane. Thus, an active carbonate ester derivative can be obtained.

(5) Conversion into Amino Group by Cyanation, Hydrogenation or Mesylation, Amination With regard to a cyano derivative, a branched polyoxyalkylene derivative having a hydroxyl group is dissolved in ion-exchange water, an aqueous potassium hydroxide solution is added under ice cooling, and acrylonitrile is reacted by adding dropwisely. After neutralization, extraction is performed with chloroform and, after concentration, crystals are precipitated with ethyl acetate and hexane. Thus, a cyano derivative can be obtained.

The cyano derivative, toluene, and a hydrogenation catalyst such as nickel are added to a high-pressure reaction apparatus and dissolved, and hydrogen is added thereto at 130° C. until 4' MPa to perform the reaction. The filtrated reaction solution can be crystallized with hexane to obtain an amino derivative.

Alternatively, the mesyl derivative obtained in (2) is dissolved in ammonia water and reacted at 60° C. After removal of ammonia by nitrogen bubbling, extraction is performed with toluene and, after concentration, crystallization is performed with toluene and hexane. Thus, an amino derivative can be obtained.

(6) Introduction of Maleimido Group by Maleamidation, Maleimidation by Ring Closure Reaction, a Maleimidation Reagent (Maleimidopropionic Acid N-Hydroxysuccinic Acid Ester, Maleimidocaproic Acid N-Hydroxysuccinic Acid Ester, or the Like)

The amino derivative obtained in (5) is dissolved in toluene and reacted with maleic anhydride, and then crystallization is performed with ethyl acetate and hexane, whereby a maleamide derivative can be obtained. It is dissolved in acetonitrile and, after sodium acetate and acetic anhydride are added thereto, they are reacted at 80° C. After filtration, the reaction solution is concentrated and crystallization is performed with ethyl acetate and hexane, whereby a maleimide derivative can be obtained.

Alternatively, the amino derivative obtained in (5) is dissolved in toluene and maleimidopropionic acid N-hydroxysuccinic acid ester is added thereto to perform the reaction. After filtration of the reaction solution, crystallization is performed with ethyl acetate and hexane. Thus, a maleimide derivative can be obtained.

(7) Introduction of Aldehyde Group by Alkyl Acetalization and Hydrolysis

The mesyl derivative obtained in (2) is dissolved in toluene, a solution obtained by dissolving sodium into 3,3-diethoxypropanol is added thereto, and they are reacted at 40° C. After the filtration of the reaction solution, crystallization is performed with ethyl acetate and hexane, whereby a propyl acetal derivative can be obtained. It is dissolved in ion-exchange water, hydrolysis is performed under an acidic condition using phosphoric acid, after extraction with chloroform, concentration is performed, the reaction solution is filtrated, and crystallization is performed with ethyl acetate and hexane, whereby a maleamide derivative can be obtained.

(8) Introduction of Acetylene Group with Acetylenation Reagent (Propargylamine or the Like)

The active carbonate ester derivative obtained in (4) is dissolved in toluene, propargylamine is reacted therewith at 40° C., and then crystallization is performed with ethyl acetate and hexane, whereby an acetylene derivative can be obtained.

(9) Introduction of Azido Group with Azidation Reagent (Such as Sodium Azide)

The mesyl derivative obtained in (2) is dissolved in toluene, sodium azide is reacted therewith at 60° C., then the reaction solution is filtrated, and crystallization is performed with ethyl acetate and hexane, whereby an azide derivative can be obtained.

Using the methods as described above, the hydroxyl group in the formula (p0) can be converted into a functional group reactive with a bio-related substance.

According to the invention, a bio-related substance modified with the polyoxyalkylene group having a multibranched structure can be obtained. The bio-related substance can afford a large hydration layer without blocking an active site since the bonded polyoxyalkylene group has a multibranched structure, and thus the substance can maintain the activity.

Moreover, since the derivative has a double-chain structure having a specific molecular weight between the functional group capable of forming a chemical bond with a bio-related substance and the multibranched structure, the reactivity between the bio-related substance and the multibranched polyoxyalkylene derivative is increased, so that a polyoxyalkylene-modified product of the bio-related substance can be efficiently obtained.

EXAMPLES

The following will describe the present invention more specifically with reference to Examples. In this regard, $^1$H-NMR analysis and hydroxyl value (OHV) were employed for analyzing and identifying the compounds in Examples.
<Analytical method of $^1$H-NMR>: in $^1$H-NMR analysis, JNM-ECP 400 manufactured by Nippon Denshi Datum K. K was employed. The integral values in NMR data are theoretical values.
<Analytical method of OHV>: in OHV analysis, measurement was carried out using the phthalic anhydride method (in accordance with JIS K1557).

For the measurement of the moisture, a Karl Fischer's moisture meter ("7S8/3-20 model" manufactured by Metrohm-Shibata) was used and "Hydranal Composite 2" (manufactured by Sigma-Aldrich) was used as a Karl Fischer's reagent.

Example 1

Synthesis of Multibranched Polyoxyalkylene Derivative (1) (Case of R=Methyl Group, A$^1$O, A$^2$O=Oxyethylene Group, n=114, m=170, and Molecular Weight=about 40,000)

Example 1-1

To a 2 L four-neck flask fitted with a thermometer, a nitrogen-introducing tube, and a stirrer were added 1050.0 g (7.94 mol) of 2,2-dimethyl-1,3-dioxolane-4-methanol (IPG) obtained by distillation of Solketal [manufactured by ALDRICH] and 1050.0 g of dry toluene. With stirring and introducing nitrogen, 36.5 g (1.59 mol) of sodium was added portionwise to obtain a solution of IPG sodium product (IPG-Na)/toluene. IPG 3.78 mmol/g, sodium 0.76 mmol/g.

Example 1-2

To a 1000 ml round-bottom flask fitted with a thermometer, a nitrogen-introducing tube, and a stirrer were added 132.2 g (1.0 mol) of 2,2-dimethyl-1,3-dioxolane-4-methanol, 231.4 g (1.2 mol) of a 28% methanol solution of sodium methoxide, and 500 ml of toluene. With introducing nitrogen thereinto, the toluene was refluxed under reduced pressure for 1 hour to remove the methanol by distillation. With maintaining the solution at 80° C., 126.6 g (1.0 mol) of benzyl chloride was added dropwise over a period of 2 hours using a dropping funnel, followed by further 2 hours of the reaction. The reaction solution was subjected to solvent removal and purification by distillation (b.p. 93-95° C./266 Pa) to obtain 4-(benzyloxymethyl)-2,2-dimethyl-1,3-dioxolane.
$^1$H-NMR (CDCl$_3$, internal standard: TMS) δ (ppm): 1.36, 1.42 (3H, 3H, s, C(C$\underline{H}_3$)$_2$), 3.45-3.57 (2H, m, C$\underline{H}_2$O—C(CH$_3$)$_2$), 3.73-3.76 (1H, m, C$\underline{H}$O—C(CH$_3$)$_2$), 4.03-4.07, 4.28-4.32 (2H, m, C$\underline{H}_2$O—CH$_2$Ph), 4.57 (2H, q, —C$\underline{H}_2$Ph), 7.15-7.40 (5H, m, —CH$_2$P$\underline{h}$) (Ph Represents a Phenyl Group)

Example 1-3

Into a 1 L beaker were weighed 222 g (1.0 mol) of 4-(benzyloxymethyl)-2,2-dimethyl-1,3-dioxolane prepared in 1-2, 250 ml of ethanol, and 400 ml of distilled water, and the whole was adjusted to pH 2 with phosphoric acid. With introducing nitrogen thereinto, the solution was heated to 70° C. After 1.5 hours of the reaction, the solution was adjusted to pH 7.0 with sodium hydroxide. The resulting salt was subjected to adsorption treatment with an adsorbent "KYOWAAD 1000" (manufactured by Kyowa Hakko Kogyo Co., Ltd.) and then subjected to solvent removal to obtain 3-benzyloxy-1,2-propanediol.
$^1$H-NMR (CDCl$_3$, internal standard: TMS) δ (ppm): 3.50-3.71 (4H, m, C$\underline{H}_2$OH, C$\underline{H}_2$O—CH$_2$Ph), 3.86-3.91 (1H, m, C$\underline{H}$OH), 4.54 (2H, m, —C$\underline{H}_2$Ph), 7.27-7.38 (5H, m, —CH$_2$P$\underline{h}$).

Example 1-4

To a 300 ml round-bottom flask fitted with a thermometer, a nitrogen-introducing tube, and a stirrer were added 27.3 g (0.15 mol) of 3-benzyloxy-1,2-propanediol, 127 g of dry toluene, and 0.9 g (39 mmol:26 mol %) of metallic sodium. With introducing nitrogen thereinto, the whole was stirred at room temperature until the metallic sodium was dissolved. The solution was charged into a 5 L autoclave and inside of the system was replaced by nitrogen, followed by heating to 100° C. Then, 1473 g (33.5 mol) of ethylene oxide was added thereto at 100 to 150° C. under a pressure of 1 MPa or lower, followed by continuation of the reaction for another 1 hour. After unreacted ethylene oxide gas was removed under reduced pressure, the residue was cooled to 60° C. and adjusted to pH 7.5 with a 85% aqueous phosphoric acid solution to obtain the following compound (p1).

$^1$H-NMR (CDCl$_3$, internal standard: TMS) δ (ppm): 3.40-3.80 (901H, m, —CH$_2$O(CH$_2$CH$_2$O)$_m$H, CHO(CH$_2$CH$_2$O)$_m$H, CH$_2$OCH$_2$Ph), 4.54 (2H, s, —CH$_2$Ph), 7.27-7.38 (5H, m, —CH$_2$Ph).

Molecular weight (OHV): 9,870 (m=about 112)

[Chem 25]

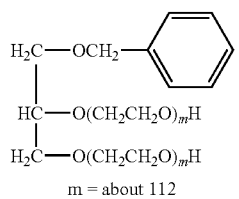

m = about 112

(p1)

Example 1-5

Into a 5 L four-neck flask fitted with a thermometer, a nitrogen-introducing tube, a stirrer, a Dean-stark tube, and a condenser tube were added 870 g of the compound (p1) prepared in 1-4, 3.0 kg of toluene, and 0.65 g of 2,6-di-tert-butyl-p-cresol and the whole was heated to 60° C. with stirring and introduction of nitrogen to perform dissolution. The resulting solution was heated to 110° C. and about 250 g of a fraction was removed as an azeotrope with toluene, thereby water removal being achieved. After cooling to 40° C., 28.8 g of triethylamine was added thereto and then 26.5 g of methanesulfonyl chloride was added dropwise thereto over a period of 30 minutes, followed by 3 hours of the reaction at 40° C.

Thereto was added 685 g of the IPG-Na/toluene solution prepared in 1-1, followed by 3 hours of the reaction at 40° C. Thereto was added 1.0 kg of a 25% by weight sodium chloride solution, and the whole was stirred at 50° C. for 15 minutes. After 15 minutes of still standing, the lower layer was removed. The washing step with water was repeated five times. The upper layer after washing with water was subjected to removal of 250 g of a fraction under slightly reduced pressure at 50° C. to perform removal of water. Further, magnesium sulfate was added and removal of water was achieved by 30 minutes of stirring. The solution was filtrated, the filtrate was collected, and 5.0 kg of n-hexane was added thereto to perform crystallization. After the crystals were collected by filtration, the crystals were washed with 5.0 kg of n-hexane. The crystals were collected by filtration and dried under vacuum to obtain 880 g of the following compound (p2).

$^1$H-NMR (CDCl$_3$, internal standard: TMS) δ (ppm): 3.40-3.80 (905H, m, —CH$_2$O(CH$_2$CH$_2$O)$_m$CH$_2$—, CHO(CH$_2$CH$_2$O)$_m$CH—, CH$_2$OCH$_2$Ph), 4.54 (2H, s, —CH$_2$Ph), 7.27-7.38 (5H, m, —CH$_2$Ph), 1.37 (12H, d, (—O—)$_2$C(—CH$_3$)$_2$), 4.05 (4H, m, —O—CH$_2$—CH(O)—CH$_2$—O—).

[Chem 26]

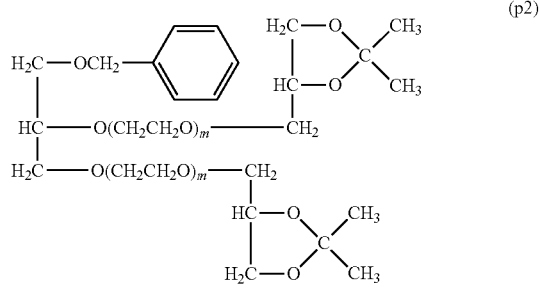

m = about 112

(p2)

Example 1-6

To a 20 L flask fitted with a thermometer, a nitrogen-introducing tube, a stirrer, and a bottom stopper were added 750 g of the compound (p2) obtained in 1-5 and 13.5 kg of ion-exchange water, and the compound was dissolved with introduction of nitrogen. Under light shielding, 85% phosphoric acid was added dropwise so that pH was adjusted to pH 1.80, followed by 3 hours of the reaction at room temperature. Thereto was added a 10N aqueous sodium hydroxide solution to achieve neutralization, then 2.7 kg of sodium chloride was added, and further pH was adjusted to 6.0 to 7.0 with a 10N aqueous sodium hydroxide solution. Extraction was performed with 2.25 L of chloroform and, after the lower layer was taken out, 1.5 L of chloroform was again added to perform extraction. The lower layers were combined and concentrated and the concentration residue was dissolved in 2.5 kg of toluene. Then, 1.9 kg of n-hexane was added to a filtrate from which insoluble matter had been filtrated off, to perform crystallization and, after the crystals were collected by filtration, the crystals were washed with 1.9 kg of n-hexane. The crystals were collected by filtration and dried under vacuum to obtain 720 g of the following compound (p3).

$^1$H-NMR (CDCl$_3$, internal standard: TMS) δ (ppm): 3.40-3.80 (909H, m, —CH$_2$O(CH$_2$CH$_2$O)$_m$CH$_2$—, CHO(CH$_2$CH$_2$O)$_m$CH$_2$—, CH$_2$OCH$_2$Ph), —O—CH$_2$—CH(O)—CH$_2$—O—), 4.54 (2H, s, —CH$_2$Ph), 7.27-7.38 (5H, m, —CH$_2$Ph).

[Chem 27]

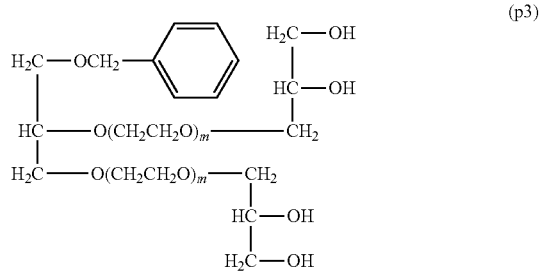

m = about 112

(p3)

Example 1-7

Into a 5 L four-neck flask fitted with a thermometer, a nitrogen-introducing tube, a stirrer, a Dean-stark tube, and a condenser tube were added 713 g of the compound (p3) prepared in 1-6 and 2850 g of toluene, the whole was refluxed at 110° C. for removal of water. After cooling to 60° C., 5.38 g of a 28% methanol solution of sodium methoxide was added dropwise thereto and then methanol was removed at 75° C. under reduced pressure. The reaction solution was added to a 5 L pressure vessel fitted with a thermometer, a nitrogen-introducing tube, and a stirrer and further toluene was removed at 95° C. under reduced pressure. After the inside of the system was replaced by nitrogen, the whole was heated to 100° C. Then, 695 g of ethylene oxide was added dropwise thereto at 100 to 150° C. under a pressure of 1 MPa or lower, followed by continuation of the reaction for another 2 hours. After 672 g of the resulting reaction product was taken out, 639 g of ethylene oxide was added dropwise thereto under a pressure of 1 MPa or lower, followed by continuation of the reaction for another 2 hours. The reaction product was added with 1230 g of toluene to dissolve. After 520 g of toluene was removed at 95° C. under reduced pressure for removal of water, 297 g of ethylene oxide was added thereto under a pressure of 1 MPa or lower, followed by continuation of the reaction for another 2 hours. After cooling to 60° C., pH was adjusted to 7.5 with an 85% aqueous phosphoric acid solution to obtain 760 g of the following compound (p4).

$^1$H-NMR (CDCl$_3$, internal standard: TMS) δ (ppm): 3.40-3.80 (3,631H, m, —C$\underline{H_2}$O(C$\underline{H_2}$C$\underline{H_2}$O)$_m$—C$\underline{H_2}$—, C$\underline{H}$O(C$\underline{H_2}$C$\underline{H_2}$O)$_m$C$\underline{H_2}$—, C$\underline{H_2}$OC$\underline{H_2}$Ph, C$\underline{H}$O(C$\underline{H_2}$—C$\underline{H_2}$O)$_n$C$\underline{H_2}$—, —C$\underline{H_2}$O(C$\underline{H_2}$C$\underline{H_2}$O)$_n$), 4.54 (2H, s, —C$\underline{H_2}$Ph), 7.27-7.38 (5H, m, —CH$_2$P$\underline{h}$).

Molecular weight (OH$\overline{V}$): 39,790 (n=about 170)

[Chem 28]

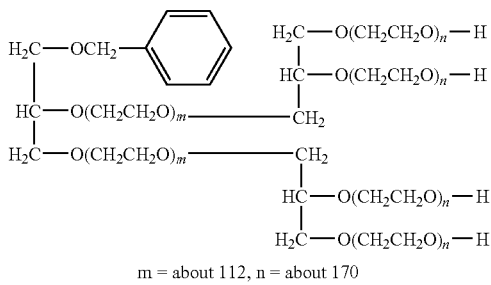

(p4)

m = about 112, n = about 170

Example 1-8

Into a 500 mL four-neck flask fitted with a thermometer, a nitrogen-introducing tube, a stirrer, a Dean-stark tube, and a condenser tube were added 150 g of the compound (p4) prepared in 1-7, 640 g of toluene, and 0.11 g of 2,6-di-tert-butyl-p-cresol and the whole was heated to 60° C. with stirring and introduction of nitrogen to perform dissolution. The resulting solution was heated to 110° C. and about 40 g of a fraction was removed as an azeotrope with toluene, thereby water removal being achieved. After cooling to 40° C., 2.54 g of triethylamine was added thereto and then 2.33 g of methanesulfonyl chloride was added dropwise thereto over a period of 10 minutes, followed by 3 hours of the reaction at 40° C.

Thereto was added 9.07 g of a 28% methanol solution of sodium methoxide, followed by 3 hours of the reaction at 40° C. Thereto was added 1.5 kg of a 25% by weight sodium chloride solution, and the whole was stirred at 50° C. for 15 minutes. After 15 minutes of still standing, the lower layer was removed. The washing step with water was repeated twice. The upper layer after washing with water was subjected to removal of 200 g of a fraction under slightly reduced pressure at 50° C. to perform removal of water. Further, magnesium sulfate was added and removal of water was achieved by 30 minutes of stirring. The solution was filtrated, the filtrate was collected, and 600 g of n-hexane was added thereto to perform crystallization. After the crystals were collected by filtration, the crystals were washed with 600 g of n-hexane. The crystals were collected by filtration and dried under vacuum to obtain 130 g of the following compound (p5).

$^1$H-NMR (CDCl$_3$, internal standard: TMS) δ (ppm): 3.40-3.80 (3,631H, m, —C$\underline{H_2}$O(C$\underline{H_2}$C$\underline{H_2}$O)$_m$C$\underline{H_2}$—, C$\underline{H}$O(C$\underline{H_2}$C$\underline{H_2}$O)$_m$C$\underline{H_2}$—, C$\underline{H_2}$OC$\underline{H_2}$Ph, C$\underline{H}$O(C$\underline{H_2}$—C$\underline{H_2}$O)$_n$C$\underline{H_2}$—, —C$\underline{H_2}$O(C$\underline{H_2}$C$\underline{H_2}$O)$_n$), 4.54 (2H, s, —C$\underline{H_2}$Ph), 7.27-7.38 (5H, m, —CH$_2$P$\underline{h}$), 3.38 (12H, s, —C$\underline{H_3}$).

[Chem 29]

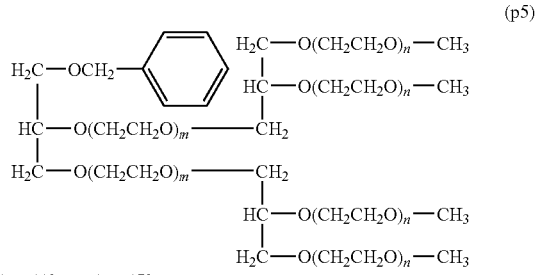

(p5)

m = about 112, n = about 170

Example 1-9

Into a 500 mL round-bottom flask fitted with a thermometer, a nitrogen-introducing tube, a stirrer, and a condenser tube were charged 120 g of the compound prepared in 1-8 (p5) and 60 g of 5% palladium carbon (50% hydrous product). After the replacement by nitrogen, 1.2 L of methanol and 200 mL of cyclohexene were added thereto and the whole was heated and gently refluxed at 52 to 55° C. to perform the reaction for 3 hours. After the reaction solution was cooled to room temperature, palladium-carbon was removed by filtration and the filtrate was concentrated. Then, 1.2 L of toluene and 1.2 L of n-hexane were added thereto to precipitate crystals. The resulting crystals were collected by filtration and dried to obtain 107 g of the following compound (p6).

$^1$H-NMR (CDCl$_3$, internal standard: TMS) δ (ppm): 3.40-3.80 (3,631H, m, —C$\underline{H_2}$O(C$\underline{H_2}$C$\underline{H_2}$O)$_m$C$\underline{H_2}$—, C$\underline{H}$O(C$\underline{H_2}$C$\underline{H_2}$O)$_m$C$\underline{H_2}$—, C$\underline{H}$O(C$\underline{H_2}$C$\underline{H_2}$O)$_n$C$\underline{H_2}$—, —C$\underline{H_2}$O(C$\underline{H_2}$C$\underline{H_2}$O)$_n$), 3.38 (12H, s, —C$\underline{H_3}$).

[Chem 30]

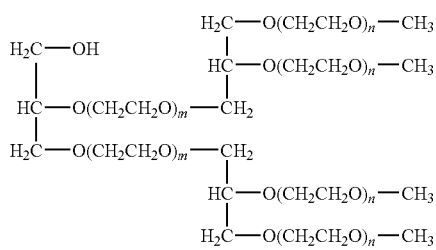

(p6)

m = about 112, n = about 170

Example 1-10

Into a 500 mL round-bottom flask fitted with a thermometer, a nitrogen-introducing tube, a stirrer, and a condenser tube were charged 50 g of the compound prepared in 1-9 (p6), 3.1 g of a 50% aqueous potassium hydroxide solution, and 50 g of ion-exchange water. After the replacement by nitrogen, they were dissolved and cooled to 10° C. and then 50 g of acrylonitrile was added, followed by 4 hours of the reaction. After the reaction solution was neutralized with phosphoric acid, 100 g of ethyl acetate was added to extract and remove impurities and then the target product was extracted and collected with 300 g of chloroform. After magnesium sulfate was added to the chloroform layer for removal of water and then removed by filtration, the filtrate was concentrated. Crystals were precipitated by adding 500 mL of ethyl acetate and 500 mL of n-hexane and the resulting crystals were collected by filtration and dried to obtain 40 g of the following compound (p7).

$^1$H-NMR (CDCl$_3$, internal standard: TMS) δ (ppm): 3.40-3.80 (3,633H, m, —CH$_2$O(CH$_2$CH$_2$O)$_m$CH$_2$—, CHO(CH$_2$CH$_2$O)$_m$CH$_2$—, CHO(CH$_2$CH$_2$O)$_n$CH$_2$—, —CH$_2$O(CH$_2$CH$_2$O)$_n$, —OCH$_2$CH$_2$CN), 3.38 (12H, s, —CH$_3$), 2.62 (2H, t, —CH$_2$CN).

[Chem 31]

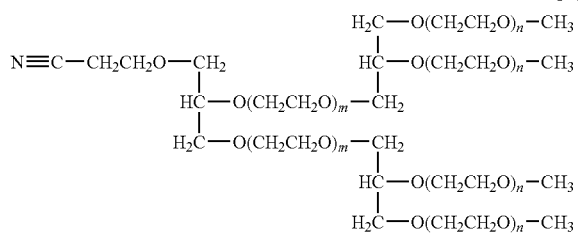

(p7)

m = about 112, n = about 170

Example 1-11

Into a 1 L pressure vessel fitted with a thermometer, a nitrogen-introducing tube, and a stirrer were added 30 g of the compound (p7) prepared in 1-10, 2.7 g of Ni catalyst, and 545 g of toluene. After the replacement by nitrogen, the whole was dissolved at 60° C., ammonia gas was added to 0.5 MPa, hydrogen gas was added to 3.5 MPa, and the whole was heated to 130° C., followed by 3 hours of the reaction. After cooling, the whole was degassed by nitrogen bubbling and, after the reaction solution was filtrated, the filtrate was concentrated. The concentrated solution was subjected to crystal precipitation by adding 300 mL of toluene and 450 mL of n-hexane. The resulting crystals were collected by filtration and dried to obtain 25 g of the following compound (p8).

$^1$H-NMR (D$_2$O, internal standard: DSS) δ (ppm): 3.40-3.80 (3,633H, m, —CH$_2$O(CH$_2$CH$_2$O)$_m$CH$_2$—, CHO(CH$_2$CH$_2$O)$_m$CH$_2$—, CHO(CH$_2$CH$_2$O)$_n$CH$_2$—, —CH$_2$O(CH$_2$CH$_2$O)$_n$, —OCH$_2$CH$_2$CN), 3.38 (12H, s, —CH$_3$), 2.80 (2H, t, —CH$_2$NH$_2$), 1.80 (2H, m, —CH$_2$CH$_2$NH$_2$).

[Chem 32]

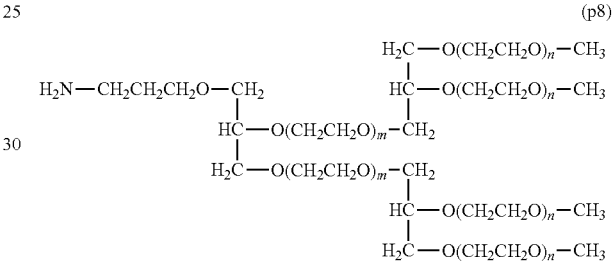

(p8)

m = about 112, n = about 170

Example 1-12

Into a 500 mL round-bottom flask fitted with a thermometer, a nitrogen-introducing tube, a stirrer, and a condenser tube were charged 15 g of the compound (p8) prepared in 1-11, 78 g of toluene, and 12 g of acetonitrile. After the replacement by nitrogen, the whole were dissolved at 40° C. and cooled to 25° C. and then 0.19 g of N-methylmorpholine and 0.15 g of maleimidopropionic acid N-hydroxysuccinic acid ester were added, followed by 5 hours of the reaction. After the reaction solution was filtrated, 150 g of ethyl acetate and 200 g of n-hexane were added to the filtrate to precipitate crystals. Further, 9 g of acetonitrile, 270 g of ethyl acetate, and 200 g of n-hexane were added to the resulting crystals to precipitate crystals. The resulting crystals were collected by filtration and dried to obtain 14 g of the following compound (p9).

$^1$H-NMR (CDCl$_3$, internal standard: TMS) δ (ppm): 3.40-3.80 (3,633H, m, —CH$_2$O(CH$_2$CH$_2$O)$_m$CH$_2$—, CHO(CH$_2$CH$_2$O)$_m$CH$_2$—, CHO(CH$_2$CH$_2$O)$_n$CH$_2$—, —CH$_2$O(CH$_2$CH$_2$O)$_n$, —OCH$_2$CH$_2$CN, —CH$_2$NHCO), 3.38 (12H, s, —CH$_3$), 2.48 (2H, t, —NHCOCH$_2$CH$_2$—), 1.75 (2H, m, —CH$_2$CH$_2$NHCO), 6.70 (2H, s, —CH═CH—).

[Chem 33]

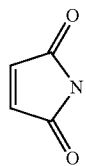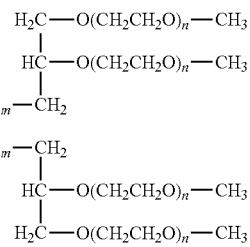

(p9)

m = about 112, n = about 170

Example 1-13

Into a 500 mL round-bottom flask fitted with a thermometer, a nitrogen-introducing tube, a stirrer, and a condenser tube were charged 15 g of the compound (p8) prepared in 1-11, 65 g of toluene, 0.0015 g of 2,6-di-tert-butyl-p-cresol, and 0.15 g of sodium acetate. After the replacement by nitrogen, the whole were dissolved at 55° C. and then 0.33 g of glutaric anhydride was added, followed by 5 hours of the reaction. Further, 0.7 g of N-hydroxysuccinimide was added to the reaction solution and, after cooling to 40° C., 1.2 g of N',N-dicyclohexylcarbodiimide was added, followed by 4 hours of the reaction. After the reaction solution was filtrated, 105 g of n-hexane was added to the filtrate to precipitate crystals. Further, 12 g of acetonitrile, 110 g of ethyl acetate, and 80 g of n-hexane were added to the resulting crystals to precipitate crystals. The resulting crystals were collected by filtration and dried to obtain 13 g of the following compound (p10).

$^1$H-NMR (CDCl$_3$, internal standard: TMS) δ (ppm): 3.40-3.80 (3,633H, m, —CH$_2$O(CH$_2$CH$_2$O)$_m$CH$_2$—, CHO(CH$_2$CH$_2$O)$_m$CH$_2$—, CHO(CH$_2$CH$_2$O)$_n$CH$_2$—, —CH$_2$O(CH$_2$CH$_2$O)$_n$, —OCH$_2$CH$_2$CN, —CH$_2$NHCO), 3.38 (12H, s, —CH$_3$), 2.7 (2H, t, —NHCOCH$_2$CH$_2$CH$_2$CO—), 2.3 (2H, t, —NHCOCH$_2$CH$_2$CH$_2$CO—), 2.1 (2H, multi, —NHCOCH$_2$CH$_2$CO—), 1.75 (2H, m, —CH$_2$CH$_2$NHCO), 2.85 (4H, s, —CH$_2$—CH$_2$—).

Example 1-14

Modification of Insulin

Using the succinimide compound (p10) obtained in Example 1-13, modification of insulin (manufactured by SEROLOGICALS CORPORATIONPN, recombinant human insulin, Mw 5800) was carried out.

Using 0.1N sodium carbonate buffer (pH=9.0), a 10 mg/ml buffer solution of insulin was prepared. After 6.9 mg of the compound of the formula (p10) was added into 100 μl of the solution, the reaction was carried out at 4° C. for 20 hours. The whole amount of the reaction solution was charged on Q-Sepharose FF (manufactured by Amersham) column and equilibrated with 20 mM Tris-HCl buffer (pH=8.2). After equilibration, a solution obtained by adding NaCl to the buffer so as to be 1N was passed through the column and a fraction of insulin modified with (p11) was obtained while the eluate was monitored by UV. After 20 μl of the fraction and 20 μl of tris-SDS sample treatment solution were mixed, the mixture was heated in a boiling water bath for 2 minutes and 30 seconds and 20 μl of the solution was subjected to sodium dodecylsulfate-polyacrylamide gel electrophoresis (4 to 20%) analysis, which showed that insulin was modified with the formula (p11). The staining was performed by CBB staining.

[Chem 34]

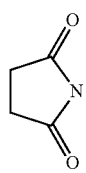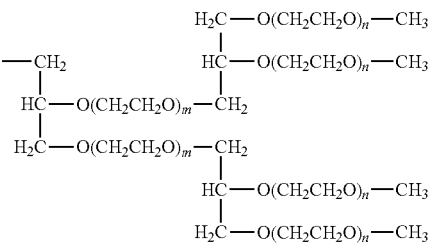

(p10)

m = about 112, n = about 170

Example 2

Synthesis of Multibranched Polyoxyalkylene Derivative (1A) (Case of R=Methyl Group, $A^1O$, $A^2O$=Oxyethylene Group, N=114, M=85, a=3, and Molecular Weight=About 40,000)

Example 2-1

To a 2 L flask fitted with a thermometer, a nitrogen-introducing tube, a stirrer, and a bottom stopper were added 100 g (0.66 mol) of xylitol [manufactured by Wako Pure Chemical Industries, Ltd.], 191.7 g of 2,2-dimethoxypropane, and 3.74 mg of p-toluenesulfonic acid monohydrate. With nitrogen bubbling, the whole was heated to 65° C. to perform the reaction until xylitol was dissolved. The whole was heated to 80° C., about 54 g of a fraction of 2,2-dimethoxypropane was removed under slightly reduced pressure, and further distillation was performed to obtain 79.4 g of the following compound, 1,2,3,4-diisopropylidenexylitol (hereinafter referred to DIXY).

$^1$H-NMR (CDCl$_3$, internal standard: TMS) δ (ppm): 1.38, 1.44 (6H, 6H, s, C(CH$_3$)$_2$), 3.58-3.67 (1H, m, CHO—C(CH$_3$)$_2$, 3.78-3.91 (2H, m, CH$_2$O—C(CH$_3$)$_2$, 3.96-4.03 (1H, m, CHO—C(CH$_3$)$_2$, 4.03-4.09 (2H, m, —CH$_2$OH) 4.18-4.24 (1H, m, CHO—C(CH$_3$)$_2$.

[Chem 35]

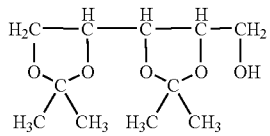

(p11)

Example 2-2

To a 2 L four-neck flask fitted with a thermometer, a nitrogen-introducing tube, and a stirrer were added 820.0 g (3.53 mol) of the compound DIXY prepared in 2-1 and 820.0 g of dry toluene. With stirring and introduction of nitrogen, 16.2 g (0.71 mol) of sodium was added portionwise and dissolved to obtain a solution of DIXY sodium product (DIXY-Na)/toluene. DIXY 2.15 mmol/g, sodium 0.43 mmol/g

Example 2-3

Into a 5 L four-neck flask fitted with a thermometer, a nitrogen-introducing tube, a stirrer, a Dean-stark tube, and a condenser tube were added 870 g of the compound (p1) prepared in 1-4, 3.0 kg of toluene, and 0.65 g of 2,6-di-tert-butyl-p-cresol and the whole was heated to 60° C. with stirring and introduction of nitrogen to perform dissolution. The resulting solution was heated to 110° C. and about 250 g of a fraction was taken out as an azeotrope with toluene, thereby removal of water being achieved. After cooling to 40° C., 28.8 g of triethylamine was added thereto and then 26.5 g of methanesulfonyl chloride was added dropwise thereto over a period of 30 minutes, followed by 3 hours of the reaction at 40° C.

Thereto was added 1210 g of the DIXY-Na/toluene solution prepared in 2-2, followed by 3 hours of the reaction at 40° C. Thereto was added 1.0 kg of a 25% by weight sodium chloride solution, and the whole was stirred at 50° C. for 15 minutes. After 15 minutes of still standing, the lower layer was removed. The washing step with water was repeated five times. The upper layer after washing with water was subjected to removal of 250 g of a fraction under slightly reduced pressure at 50° C. to perform removal of water. Further, magnesium sulfate was added and removal of water was achieved by 30 minutes of stirring. The solution was filtrated, the filtrate was collected, and 5.0 kg of n-hexane was added thereto to perform crystallization. After the crystals were collected by filtration, the crystals were washed with 5.0 kg of n-hexane. The crystals were collected by filtration and dried under vacuum to obtain 900 g of the following compound (p12).

$^1$H-NMR (CDCl$_3$, internal standard: TMS) δ (ppm): 4.54 (2H, s, —CH$_2$Ph), 7.27-7.38 (5H, m, —CH$_2$Ph), 1.37 (24H, d, (—O—)$_2$C(—CH$_3$)$_2$).

[Chem 36]

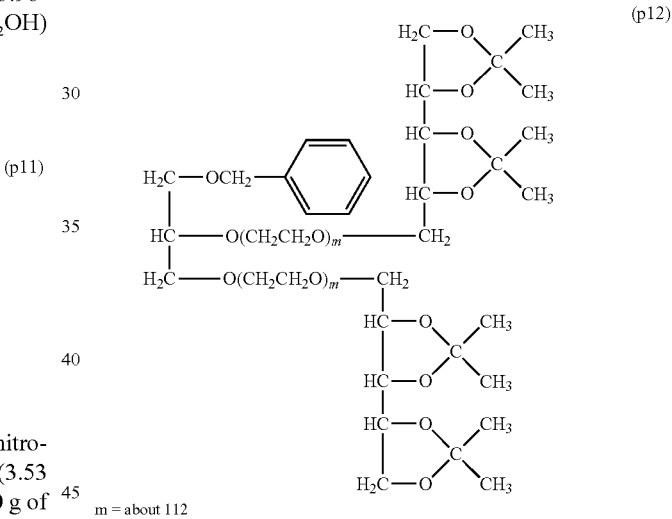

m = about 112

Example 2-4

To a 20 L flask fitted with a thermometer, a nitrogen-introducing tube, a stirrer, and a bottom stopper were added 750 g of the compound (p12) obtained in 2-3 and 13.5 kg of ion-exchange water, and the compound was dissolved with introduction of nitrogen. Under light shielding, 85% phosphoric acid was added dropwise so that pH was adjusted to pH 1.80, followed by 3 hours of the reaction at room temperature. Thereto was added a 10N aqueous sodium hydroxide solution to achieve neutralization, then 2.7 kg of sodium chloride was added, and further pH was adjusted to 6.0 to 7.0 with a 10N aqueous sodium hydroxide solution. Extraction was performed with 2.25 L of chloroform and, after the lower layer was taken out, 1.5 L of chloroform was again added to perform extraction. The lower layers were combined and concentrated and the concentration residue was dissolved in 2.5 kg of toluene. Then, 1.9 kg of n-hexane was added to a filtrate from which insoluble matter had been filtrated off, to perform crystallization and, after the crystals were collected by filtration, the crystals were washed with 1.9 kg of n-hexane. The crystals were collected by filtration and dried under vacuum to obtain 708 g of the following compound (p13).

$^1$H-NMR (CDCl$_3$, internal standard: TMS) δ (ppm): 4.54 (2H, s, —C$\underline{H}_2$Ph), 7.27-7.38 (5H, m, —CH$_2$P$\underline{h}$).

[Chem 37]

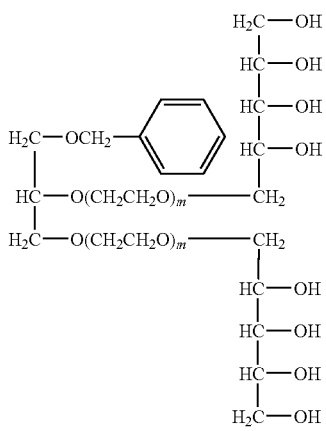

(p13)

m = about 112

Example 2-5

Into a 5 L four-neck flask fitted with a thermometer, a nitrogen-introducing tube, a stirrer, a Dean-stark tube, and a condenser tube were added 700 g of the compound (p13) prepared in 2-4 and 2850 g of toluene, the whole was refluxed at 110° C. for removal of water. After cooling to 60° C., 5.30 g of a 28% methanol solution of sodium methoxide was added dropwise thereto and then methanol was removed at 75° C. under reduced pressure. The reaction solution was added to a 5 L pressure vessel fitted with a thermometer, a nitrogen-introducing tube, and a stirrer and further toluene was removed at 95° C. under reduced pressure. After the inside of the system was replaced by nitrogen, the whole was heated to 100° C. Then, 705 g of ethylene oxide was added dropwise thereto at 100 to 150° C. under a pressure of 1 MPa or lower, followed by continuation of the reaction for another 2 hours. After 680 g of the resulting reaction product was taken out, 650 g of ethylene oxide was added dropwise thereto under a pressure of 1 MPa or lower, followed by continuation of the reaction for another 2 hours. After cooling to 60° C., pH was adjusted to 7.5 with an 85% aqueous phosphoric acid solution to obtain 770 g of the following compound (p14).

$^1$H-NMR (CDCl$_3$, internal standard: TMS) δ (ppm): 4.54 (2H, s, —C$\underline{H}_2$Ph), 7.27-7.38 (5H, m, —CH$_2$P$\underline{h}$).

Molecular weight (OHV): 40,494 (n=about 87)

[Chem 38]

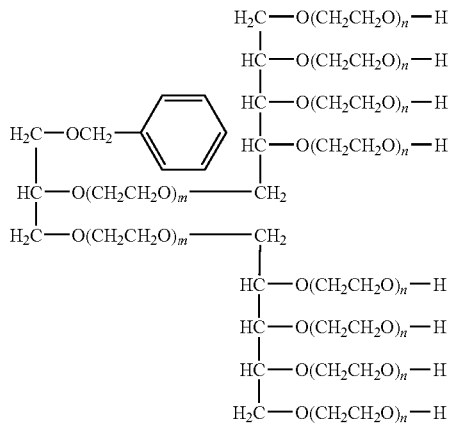

(p14)

m = about 112, n = about 87

Example 2-6

Into a 500 mL four-neck flask fitted with a thermometer, a nitrogen-introducing tube, a stirrer, a Dean-stark tube, and a condenser tube were added 150 g of the compound (p14) prepared in 2-5, 640 g of toluene, and 0.11 g of 2,6-di-tert-butyl-p-cresol and the whole was heated to 60° C. with stirring and introduction of nitrogen to perform dissolution. The resulting solution was heated to 110° C. and about 40 g of a fraction was removed as an azeotrope with toluene, thereby water removal being achieved. After cooling to 40° C., 5.08 g of triethylamine was added thereto and then 4.66 g of methanesulfonyl chloride was added dropwise thereto over a period of 10 minutes, followed by 3 hours of the reaction at 40° C.

Thereto was added 18.14 g of a 28% methanol solution of sodium methoxide, followed by 3 hours of the reaction at 40° C. Thereto was added 1.5 kg of a 25% by weight sodium chloride solution, and the whole was stirred at 50° C. for 15 minutes. After 15 minutes of still standing, the lower layer was removed. The washing step with water was repeated twice. The upper layer after washing with water was subjected to removal of 200 g of a fraction under slightly reduced pressure at 50° C. to perform removal of water. Further, magnesium sulfate was added and removal of water was achieved by 30 minutes of stirring. The solution was filtrated, the filtrate was collected, and 600 g of n-hexane was added thereto to perform crystallization. After the crystals were collected by filtration, the crystals were washed with 600 g of n-hexane. The crystals were collected by filtration and dried under vacuum to obtain 120 g of the following compound (p15).

$^1$H-NMR (CDCl$_3$, internal standard: TMS) δ (ppm): 4.54 (2H, s, —C$\underline{H}_2$Ph), 7.27-7.38 (5H, m, —CH$_2$P$\underline{h}$), 3.38 (24H, s, —C$\underline{H}_3$).

[Chem 39]

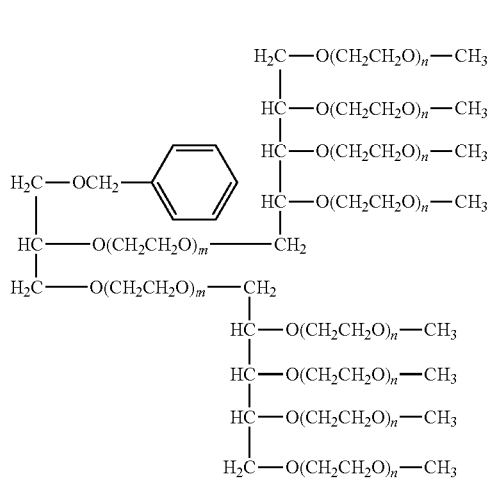

(p15)

m = about 112, n = about 87

Example 2-7

Into a 500 mL round-bottom flask fitted with a thermometer, a nitrogen-introducing tube, a stirrer, and a condenser tube were charged 120 g of the compound prepared in 2-6 (p15) and 60 g of 5% palladium carbon (50% hydrous product). After the replacement by nitrogen, 1.2 L of methanol and 200 mL of cyclohexene were added thereto and the whole was heated and gently refluxed at 52 to 55° C. to perform the reaction for 3 hours. After the reaction solution was cooled to room temperature, palladium-carbon was removed by filtration and the filtrate was concentrated. Then, 1.2 L of toluene and 1.2 L of n-hexane were added thereto to precipitate crystals. The resulting crystals were collected by filtration and dried to obtain 112 g of the following compound (p16).

$^1$H-NMR (CDCl$_3$, internal standard: TMS) δ (ppm): 3.38 (24H, s, —CH$_3$).

[Chem 40]

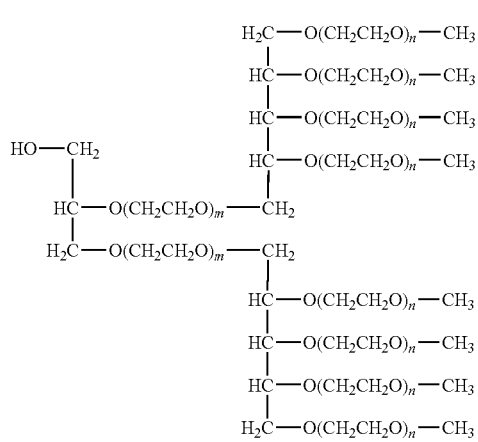

(p16)

m = about 112, n = about 87

Example 2-8

Into a 500 mL round-bottom flask fitted with a thermometer, a nitrogen-introducing tube, a stirrer, and a condenser tube were charged 50 g of the compound (p16) prepared in 2-7, 3.1 g of a 50% aqueous potassium hydroxide solution, and 50 g of ion-exchange water. After the replacement by nitrogen, the whole were dissolved and cooled to 10° C. and then 50 g of acrylonitrile was added, followed by 4 hours of the reaction. After the reaction solution was neutralized with phosphoric acid, 100 g of ethyl acetate was added to extract and remove impurities and then the target product was extracted and collected with 300 g of chloroform. After magnesium sulfate was added to the chloroform layer for removal of water and then was removed by filtration, the filtrate was concentrated. Crystals were precipitated by adding 500 mL of ethyl acetate and 500 mL of n-hexane, and the resulting crystals were collected by filtration and dried to obtain 45 g of the following compound (p17).

$^1$H-NMR (CDCl$_3$, internal standard: TMS) δ (ppm): 3.38 (24H, s, —CH$_3$), 2.62 (2H, t, —CH$_2$CN).

[Chem 41]

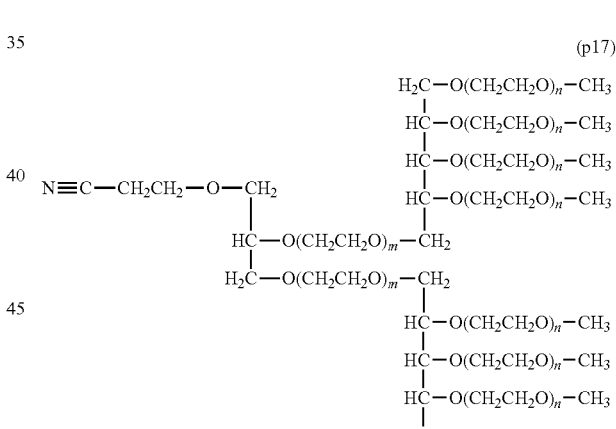

(p17)

m = about 112, n = about 87

Example 2-9

Into a 1 L pressure vessel fitted with a thermometer, a nitrogen-introducing tube, and a stirrer were added 30 g of the compound (p17) prepared in 2-8, 2.7 g of Ni catalyst, and 545 g of toluene. After the replacement by nitrogen, the whole was dissolved at 60° C., ammonia gas was added to 0.5 MPa, hydrogen gas was added to 3.5 MPa, and the whole was heated to 130° C., followed by 3 hours of the reaction. After cooling, the whole was degassed by nitrogen bubbling and, after the reaction solution was filtrated, the filtrate was concentrated. The concentrated solution was subjected to crystal precipitation by adding 300 mL of toluene and 450 mL of n-hexane. The resulting crystals were collected by filtration and dried to obtain 24 g of the following compound (p18).

$^1$H-NMR (D$_2$O, internal standard: DSS) δ (ppm): 3.38 (24H, s, —C$\underline{H}_3$), 2.80 (2H, t, —C$\underline{H}_2$NH$_2$), 1.80 (2H, m, —C$\underline{H}_2$CH$_2$N$\underline{H}_2$).

ment by nitrogen, the whole were dissolved at 40° C. and cooled to 25° C. and then 0.19 g of N-methylmorpholine and 0.15 g of maleimidopropionic acid N-hydroxysuccinic acid ester were added, followed by 5 hours of the reaction. After the reaction solution was filtrated, 150 g of ethyl acetate and 200 g of n-hexane were added to the filtrate to precipitate crystals. Further, 9 g of acetonitrile, 270 g of ethyl acetate, and 200 g of n-hexane were added to the resulting crystals to precipitate crystals. The resulting crystals were collected by filtration and dried to obtain 13 g of the following compound (p19).

$^1$H-NMR (CDCl$_3$, internal standard: TMS) δ (ppm): 3.38 (24H, s, —C$\underline{H}_3$), 2.48 (2H, t, —NHCOC$\underline{H}_2$CH$_2$—), 1.75 (2H, m, —C$\underline{H}_2$CH$_2$NHCO), 6.70 (2H, s, —C$\underline{H=CH}$—).

[Chem 43]

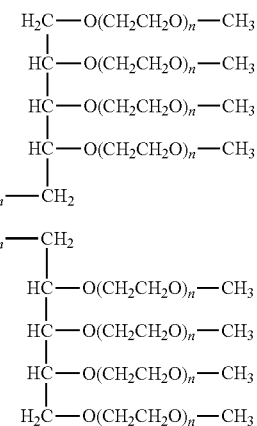

(p19)

m = about 112, n = about 87

[Chem 42]

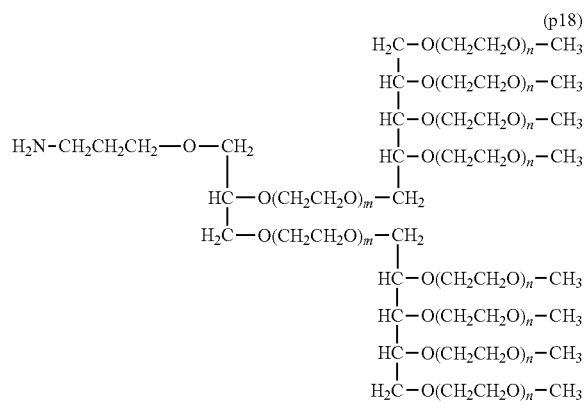

(p18)

m = about 112, n = about 87

Example 2-10

Into a 500 mL round-bottom flask fitted with a thermometer, a nitrogen-introducing tube, a stirrer, and a condenser tube were charged 15 g of the compound (p18) prepared in 2-9, 78 g of toluene, and 12 g of acetonitrile. After the replace- Example 2-11

Into a 500 mL round-bottom flask fitted with a thermometer, a nitrogen-introducing tube, a stirrer, and a condenser tube were charged 15 g of the compound (p18) prepared in 2-9, 65 g of toluene, 0.0015 g of 2,6-di-tert-butyl-p-cresol, and 0.15 g of sodium acetate. After the replacement by nitrogen, the whole were dissolved at 55° C. and then 0.33 g of glutaric anhydride was added, followed by 5 hours of the reaction. Further, 0.7 g of N-hydroxysuccinimide was added to the reaction solution and, after cooling to 40° C., 1.2 g of N',N-dicyclohexylcarbodiimide was added, followed by 4 hours of the reaction. After the reaction solution was filtrated, 105 g of n-hexane was added to the filtrate to precipitate crystals. Further, 12 g of acetonitrile, 110 g of ethyl acetate, and 80 g of n-hexane were added to the resulting crystals to precipitate crystals. The resulting crystals were collected by filtration and dried to obtain 13 g of the following compound (p20).

$^1$H-NMR (CDCl$_3$, internal standard: TMS) δ (ppm): 3.38 (24H, s, —C$\underline{H}_3$), 2.7 (2H, t, —NHCOC$\underline{H}_2$CH$_2$CH$_2$CO—), 2.3 (2H, t, —NHCOCH$_2$CH$_2$C$\underline{H}_2$CO—), 2.1 (2H, multi, —NHCOCH$_2$C$\underline{H}_2$CH$_2$CO—), 1.75 (2H, m, —C$\underline{H}_2$CH$_2$NHCO), 2.85 (4H, s, —C$\underline{H}_2$—C$\underline{H}_2$—).

[Chem 44]

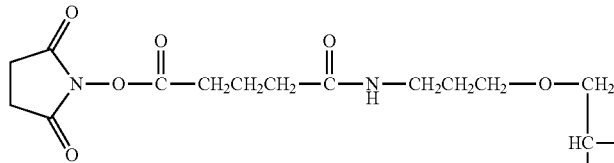 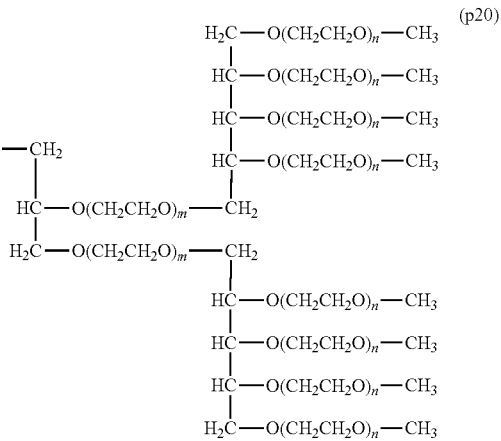

(p20)

m = about 112, n = about 87

Example 2-12

Modification of Insulin

Using the succinimide compound (p20) obtained in Example 2-11, modification of insulin (manufactured by SEROLOGICALS CORPORATIONPN, recombinant human insulin, Mw 5800) was carried out.

Using 0.1N sodium carbonate buffer (pH=9.0), a 10 mg/ml buffer solution of insulin was prepared. After 6.9 mg of the compound of the formula (p20) was added into 100 μl of the solution, the reaction was carried out at 4° C. for 20 hours. The whole amount of the reaction solution was charged on Q-Sepharose FF (manufactured by Amersham) column and equilibrated with 20 mM Tris-HCl buffer (pH=8.2). After equilibration, a solution obtained by adding NaCl to the buffer so as to be 1N was passed through the column and a fraction of insulin modified with (p20) was obtained while the eluate was monitored by UV. After 20 μl of the fraction and 20 μl of tris-SDS sample treatment solution were mixed, the solution was heated in a boiling water bath for 2 minutes and 30 seconds and 20 μl of the solution was subjected to sodium dodecylsulfate-polyacrylamide gel electrophoresis (4 to 20%) analysis, which showed that insulin was modified with the formula (p20). The staining was performed by CBB staining.

(Measurement of Viscosity)

Using the compound (p6) obtained in Example 1-9 and the compound (p16) obtained in Example 2-7, measurement of viscosity was performed. As a comparative compound, SUNBRIGHT MEH-40T, a di-branched PEG having a molecular weight of 40,000 synthesized in accordance with Example 16 of JP-A-2004-197077 was used.

The measurement of viscosity was specifically performed as follows.

Using dimethylsulfoxide, a 10% solution of each sample was prepared. One mL of the solution was charged into a sample cup of an E-type viscometer RE-105 (manufactured by TOKI) heated to 40° C. in a low-temperature constant-temperature water bath, the cup was placed in the viscometer, and then the measurement of viscosity was performed. The results are shown in the following Table 1.

TABLE 1

|  | Number of branches | Viscosity (mPa · s) |
| --- | --- | --- |
| Compound (p6) | 4 | 23.9 |
| Compound (p16) | 8 | 18.8 |
| SUNBRIGHT MEH-40T | 1 | 57.4 |
| Di-branched PEG | 2 | 50.3 |

As is apparent from Table 1, since the compounds obtained by the invention can reduce viscosity by increasing branches, not only any problem does not occur in the production method but also the improvement of operability can be expected at the time when the compound is used for the modification of a bio-related substance.

While the invention has been described in detail and with reference to specific embodiments thereof, it will be apparent to one skilled in the art that various changes and modifications can be made therein without departing from the spirit and scope thereof.

The present application is based on Japanese Patent Application No. 2007-50782 filed on Feb. 28, 2007, and the contents are incorporated herein by reference.

Also, all the references are incorporated as a whole.

INDUSTRIAL APPLICABILITY

The multibranched polyoxyalkylene derivative (1A) can afford a large hydration layer with maintaining an active site of a bio-related substance since the derivative has a multibranched structure, so that a bio-related substance modified with the derivative hardly decreases the activity and a sufficient pharmaceutical effect can be obtained. Moreover, the polyoxyalkylene derivative can reduce viscosity by increasing the branches and can be produced in good purity since any problem in the production method does not occur. Furthermore, by reducing the viscosity, the handling at the time when used for the modification of the bio-related substance becomes easy.

Therefore, the derivative can be significantly utilized for medicaments using the bio-related substance as an active substance.

The invention claimed is:

1. A polyoxyalkylene derivative represented by the formula (1A):

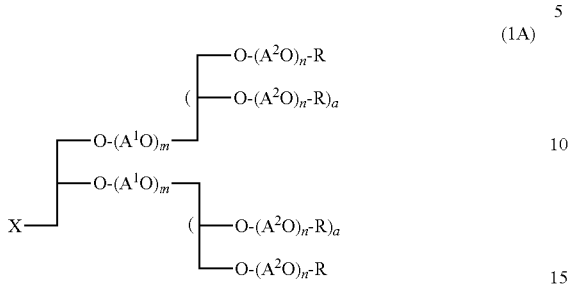

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, X represents a functional group reactive with a bio-related substance, and a represents 1, 3, or 5.

2. A polyoxyalkylene derivative represented by the formula (1):

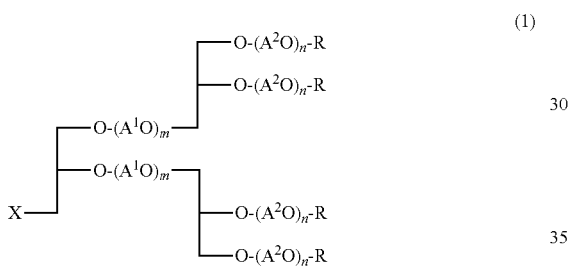

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, and X represents a functional group reactive with a bio-related substance.

3. A bio-related substance modified by a reaction with the polyoxyalkylene derivative represented by the formula (1A) of claim 1.

4. A polyoxyalkylene derivative represented by the formula (1B):

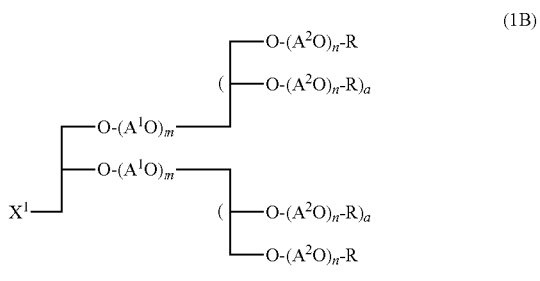

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, $X^1$ represents a hydroxyl group which may be protected, and a represents 1, 3, or 5.

5. A polyoxyalkylene derivative represented by the formula (A):

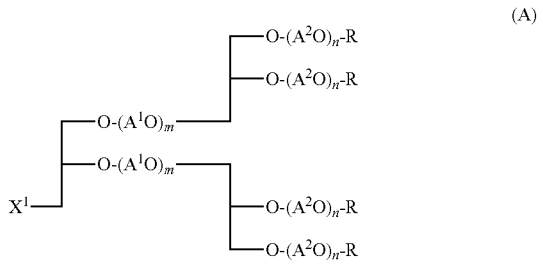

wherein $A^1O$ and $A^2O$ independently represent an oxyalkylene group having 2 to 4 carbon atoms, m represents 20 to 500, n represents 15 to 700, R represents a hydrogen atom or a hydrocarbon group having 1 to 20 carbon atoms, and $X^1$ represents a hydroxyl group which may be protected.

* * * * *